(12) United States Patent
Wang et al.

(10) Patent No.: US 12,076,320 B2
(45) Date of Patent: Sep. 3, 2024

(54) DIARYLPYRAZOLE COMPOUND, COMPOSITION COMPRISING SAME, AND USE THEREOF

(71) Applicant: Shenzhen TargetRx, Inc., Guangdong (CN)

(72) Inventors: Yihan Wang, Guangdong (CN); Zhiqiang Liu, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 333 days.

(21) Appl. No.: 17/259,472

(22) PCT Filed: Jul. 9, 2019

(86) PCT No.: PCT/CN2019/095169
§ 371 (c)(1),
(2) Date: Jan. 11, 2021

(87) PCT Pub. No.: WO2020/011141
PCT Pub. Date: Jan. 16, 2020

(65) Prior Publication Data
US 2021/0283132 A1    Sep. 16, 2021

(30) Foreign Application Priority Data
Jul. 12, 2018 (CN) .................. 201810764742.X

(51) Int. Cl.
| A61K 31/506 | (2006.01) |
| A61K 45/06 | (2006.01) |
| A61P 35/00 | (2006.01) |
| C07D 403/04 | (2006.01) |

(52) U.S. Cl.
CPC .......... *A61K 31/506* (2013.01); *A61K 45/06* (2013.01); *A61P 35/00* (2018.01); *C07D 403/04* (2013.01); *C07B 2200/05* (2013.01); *C07B 2200/13* (2013.01)

(58) Field of Classification Search
CPC ....... A61K 31/506; A61K 45/06; A61P 35/00; C07D 403/04; C07B 2200/05; C07B 2200/13
See application file for complete search history.

(56) References Cited

U.S. PATENT DOCUMENTS

| | | | | |
|---|---|---|---|---|
| 6,221,335 B1 * | 4/2001 | Foster | ........ | C07B 59/002 424/1.81 |
| 6,440,710 B1 * | 8/2002 | Keinan | ........ | C12P 13/02 435/188.5 |
| 6,603,008 B1 * | 8/2003 | Ando | ........ | A61P 25/00 546/271.4 |
| 7,517,990 B2 * | 4/2009 | Ito | ........ | C07D 233/56 546/184 |
| 8,129,394 B2 | 3/2012 | Hunag et al. | | |
| 9,850,230 B2 * | 12/2017 | Huang | ........ | A61K 45/06 |
| 2007/0082929 A1 * | 4/2007 | Gant | ........ | A61P 43/00 546/273.7 |
| 2007/0197695 A1 * | 8/2007 | Potyen | ........ | C08K 5/55 524/110 |

(Continued)

FOREIGN PATENT DOCUMENTS

| CN | 102015686 A | 4/2011 |
| CN | 102725283 A | 10/2012 |

(Continued)

OTHER PUBLICATIONS

Pubchem CID 50922675, National Center for Biotechnology Information. PubChem Compound Summary for CID 50922675. https://pubchem.ncbi.nlm.nih.gov/compound/Encorafenib. Accessed Nov. 18, 2022, create date Mar. 23, 2011. (Year: 2011).*

(Continued)

*Primary Examiner* — Joseph R Kosack
*Assistant Examiner* — Jed A Kucharczk
(74) *Attorney, Agent, or Firm* — Wolf, Greenfield & Sacks, P.C.

(57) ABSTRACT

The present invention provides a diarylpyrazole compound, a composition comprising same, and a use thereof. The diarylpyrazole compound refers to the compound represented by a formula (I) or a tautomer, a stereoisomer, a prodrug, a crystalline form, a pharmaceutically acceptable salt thereof, a hydrate, or a solvent compound. The compound and the composition of the present invention can be used for treating BRAF kinase mutant proliferative diseases and have better pharmacokinetic properties.

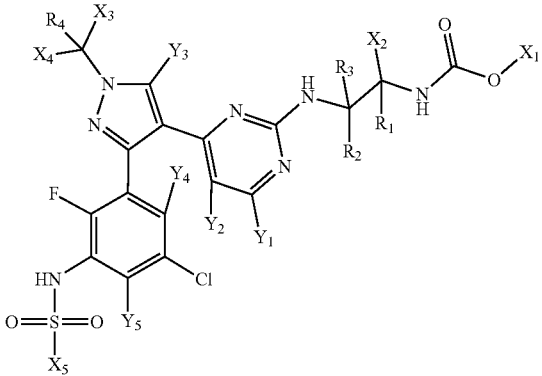

Formula (I)

9 Claims, No Drawings

(56) References Cited

U.S. PATENT DOCUMENTS

2014/0275136 A1  9/2014  Stuart et al.

FOREIGN PATENT DOCUMENTS

| CN | 103917236 A | 7/2014 |
|---|---|---|
| WO | WO 2011/025927 A1 | 3/2011 |

OTHER PUBLICATIONS

Dyck, "Effects of Deuterium Substitution on the Catabolism of P-Phenylethylamine: An In Vivo Study" Journal of Neurochemistry vol. 46 Issue 2, pp. 399-404 (Year: 1986).*
Tonn, "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes" Biological Mass Spectrometry vol. 22 Issue 11, pp. 633-642 (Year: 1993).*
Haskins, "The Application of Stable Isotopes in Biomedical Research" Biomedical Spectrometry vol. 9 Issue 7, pp. 269-277 (Year: 1982).*
Browne, "Stable Isotope Techniques in Early Drug Development: An Economic Evaluation" Journal of Clinical Pharmacology 1998; 38: 213-220 (Year: 1998).*
Baillie, "The Use of Stable Isotopes in Pharmacological Research" Pharmacology Rev. 1981; 33: 81-132 (Year: 1981).*
Gouyette, "Synthesis of Deuterium-labelled Elliptinium and its Use in Metabolic Studies" Biomedical and Environmental Mass Spectrometry, vol. 15, 243-247 (Year: 1988).*
Cherrah, "Study of Deuterium Isotope Effects on Protein Binding by Gas Chromatography/Mass Spectrometry. Caffeine and Deuterated Isotopomers" Biomedical and Environmental Mass Spectrometry vol. 14 Issue 11, pp. 653-657 (Year: 1987).*
Pieniaszek, "Moricizine Bioavailability via Simultaneous, Dual, Stable Isotope Administration: Bioequivalence Implications" J Clin Pharmacol. 1999; 39: 817-825 (Year: 1999).*
Honma et al., "The Metabolism of Roxatidine Acetate Hydrochloride" Drug Metab Dispos 15 (4): 551 (Year: 1987).*
Braftovitm (encorafenib) FDA Package Insert, Jun. 2018 (Year: 2018).*
NDA Multi-Disciplinary Review and Evaluation for Braftovitm (encorafenib), Jun. 2018 (Year: 2018).*
Liu et al., "Improving metabolic stability with deuterium: The discovery of HWL-066, a potent and long-acting free fatty acid receptor 1 agonists" Chem Biol Drug Des. 2018; 92:1547-1554. (Year: 2017).*
FDA "FDA approved encorafenib and binimetinib in combination for unresectable or metastatic melanoma with BRAF mutations" Jun. 27, 2018 (Year: 2018).*
PCT/CN2019/095169, Sep. 27, 2019, International Search Report and Written Opinion and English translations thereof.
PCT/CN2019/095169, Jan. 21, 2021, International Preliminary Report on Patentability and English translation thereof.
Extended European Search Report for Application No. 19833208.2, mailed Jul. 13, 2021.
No Author Listed, PubChem CID 50922675. Encorafenib. 34 pages.
Kushner et al., Pharmacological uses and perspectives of heavy water and deuterated compounds. Can J Physiol Pharmacol. Feb. 1999;77(2):79-88.
International Search Report and Written Opinion for Application No. PCT/CN2019/095169, mailed Sep. 27, 2019.
International Preliminary Report on Patentability No. PCT/CN2019/095169, mailed Jan. 21, 2021.
Harbeson et al., Deuterium Medicinal Chemistry: A New Approach to Drug Discovery and Development. MedChem News. May 31, 2014; 2:8-22.
Declaration under 37 CFR § 1.132 for Vinita Uttamsingh, dated Feb. 1, 2012. 3 pages.
Harbeson et al., Chapter 24—Deuterium in Drug Discovery and Development. Annual Reports in Medicinal Chemistry. 2011; 46: 403-417.
Shao et al., Derivatives of tramadol for increased duration of effect. Bioorg Med Chem Lett. Feb. 2006;16(3):691-4. doi: 10.1016/j.bmcl. 2005.10.024. Epub Oct. 27, 2005.

* cited by examiner

DIARYLPYRAZOLE COMPOUND, COMPOSITION COMPRISING SAME, AND USE THEREOF

CROSS REFERENCE TO RELATED APPLICATIONS

The present application is a national application of PCT/CN2019/095169 filed on Jul. 9, 2019, which claims the priority of the Chinese Patent Application No. 201810764742.X filed on Jul. 12, 2018. The Chinese Patent Application No. 201810764742.X is incorporated herein by reference as part of the disclosure of the present application.

FIELD OF THE INVENTION

The present disclosure relates to the field of pharmaceutical technology, particularly relates to a diarylpyrazole compound, a composition comprising the same and use thereof. More specifically, the present disclosure relates to some deuterated methyl (1-((4-(3-(5-chloro-2-fluoro-3-(methylsulfonamido)phenyl)-1-isopropyl-1H-pyrazol-4-yl)pyr imidin-2-yl)amino)propan-2-yl)carbamate compounds. These deuterated compounds and compositions thereof can be used in the treatment of proliferative diseases caused by BRAF kinase mutations, with better pharmacokinetic and/or pharmacodynamic properties.

BACKGROUND OF THE INVENTION

Mitogen-activated protein kinase (MAPK) pathway mediates the activity of many effector molecules that coordinate and control the proliferation, survival, differentiation and migration of cells. Cells are stimulated by, for example, growth factors, cytokines, or hormones, resulting in the binding of plasma membrane associated Ras to GTP and thereby being activated to recruit Raf. This interaction induces the kinase activity of Raf, leading to the direct phosphorylation of MAPK/ERK (MEK), which in turn phosphorylates extracellular signal-related kinase (ERK). The activated ERR phosphorylates a series of effector molecules, such as kinases, phosphatases transcription factors and cytoskeleton proteins. Therefore, the Ras-Raf-MEK-ERK signaling pathway transmits signals from cell surface receptors to the nucleus, and is essential in cell proliferation and survival.

According to the ability to interact with the upstream regulator Ras, Raf has three different isotypes, namely A-Raf, B-Raf and C-Raf Activating mutations of one of the Ras genes can be observed in approximately 20% of all tumors, and the Ras-Raf-MEK-ERK pathway is activated in approximately 30% of all tumors. Activating mutations in the B-Raf kinase domain occur in approximately 70% of melanoma, 40% of papillary carcinoma, 30% of low-grade ovarian cancer, and 10% of colorectal cancer. Most of B-Raf mutations are found in the kinase domain, of which single substitution (V600E) accounts for 80%. The mutant B-Raf protein activates the Raf-EK-ERK pathway by targeting the increased kinase activity of MEK or by activating C-Raf. B-Raf inhibitors inhibit cells involving B-Raf kinase by blocking the signal cascades in these cancer cells and ultimately inducing the cell cycle arrest and/or death.

Encorafenib (also known as LGX-818, its chemical name is (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate, with the following structural formula) is a novel oral BRAF inhibitor jointly developed by Novartis and Array BioPharma, which can inhibit the activation of MAPK pathway caused by B-Raf kinase mutations (such as V600 mutations, that are, glutamic acid mutations at amino acid 600). Encorafenib alone or in combination with the MEK inhibitor Binimetinib is used in the treatment of patients with advanced $BRAF^{V600}$ mutant melanoma. On Jun. 27, 2018, FDA approved Encorafenib (commercial name is BRAFTOVI) capsules in combination with Binimetinib (commercial name is MEKTOVI) tablets for the treatment of melanoma patients with $BRAF^{V600E}$ or $BRAF^{V600}x$ mutation.

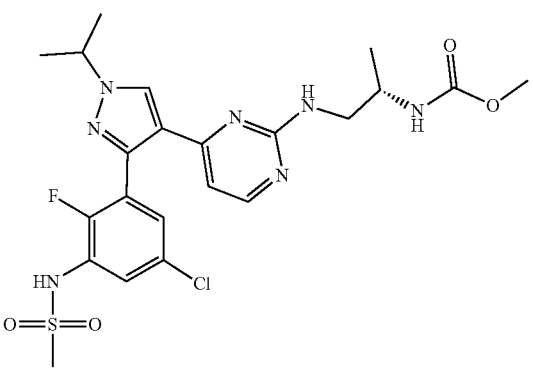

Encorafenib

Poor absorption, distribution, metabolism, and/or excretion (ADME) properties are known to be the primary causes of clinical trial failure of many drug candidates. At present, many marketed drugs have limitations on their application due to their poor ADME properties. The rapid metabolism makes many drugs, which could have been effective in treating diseases otherwise, difficult to be used as drugs due to their rapid clearance from the body. Although a frequent or high-dose administration may solve the problem of rapid drug clearance, this approach will bring about problems such as poor compliance of patients, side effects caused by high-dose administration, and increased treatment costs. In addition, drugs that are rapidly metabolized may also expose the patients to undesirable toxic or reactive metabolites.

Although Encorafenib as a BRAF inhibitor can effectively treat melanoma with BRAF V600 mutations, there are still serious unmet clinical needs in this field. Moreover, the Encorafenib compound is a type II BCS compound with poor water-solubility at weakly acidic and neutral pH, and the oral availability is very poor, so it is still a challenging work to discover novel compounds that can treat diseases caused by BRAF kinase mutations with good oral bioavailability and druggability. Therefore, it is still necessary in this field to develop compounds that are suitable for use as BRAF inhibitors with selective inhibitory activity and/or better pharmacodynamics/pharmacokinetics. The present disclosure provides such compounds.

SUMMARY OF THE INVENTION

In view of the above technical problems, the present disclosure provides a novel deuterated diarylpyrazole compound, a composition comprising the same and use thereof. The compounds have better BRAF kinase inhibitory activity, higher inhibitory activity and selectivity against V600 mutations (such as V600E and V600K), lower side effects, and better pharmacokinetic properties, and can be used in the treatment of proliferative diseases caused by BRAF kinase mutations.

As used herein, the term "compound of the present disclosure" (or "compound disclosed herein") refers to the compounds represented by formulae (I) to (III) (including subsets, such as formula (Ia)). The term also includes tautomers, stereoisomers, prodrugs, crystal forms, pharmaceutically acceptable salts, hydrates or solvates thereof.

In this regard, the technical solutions adopted by the present disclosure are as follows:

In the first aspect, the present disclosure provides a compound of formula (I):

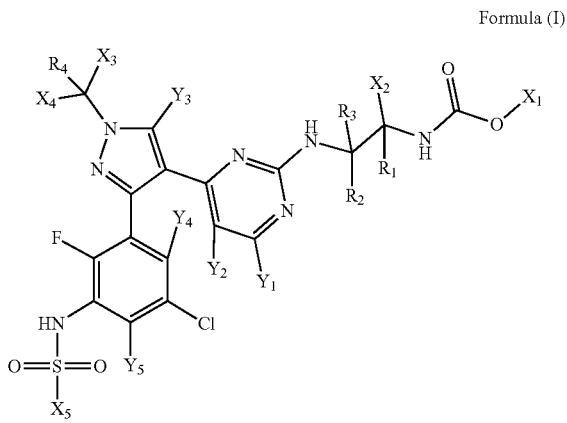

Formula (I)

wherein,
$Y_1$, $Y_2$, $Y_3$, $Y_4$ and $Y_5$ are each independently selected from hydrogen, deuterium, halogen or trifluoromethyl;
$R_1$, $R_2$, $R_3$ and $R_4$ are each independently selected from hydrogen or deuterium;
$X_1$, $X_2$, $X_3$, $X_4$ and $X_5$ are each independently selected from $CH_3$, $CD_3$, $CHD_2$ or $CH_2D$;
with the proviso that the compound described above contains at least one deuterium atom;
or a tautomer, stereoisomer, prodrug, crystal form, pharmaceutically acceptable salt, hydrate or solvate thereof.

In another aspect, the present disclosure provides a pharmaceutical composition, which comprises the compound of the present disclosure and pharmaceutically acceptable excipient(s). In a specific embodiment, the compound of the present disclosure is provided in an effective amount in the pharmaceutical composition. In a specific embodiment, the compound of the present disclosure is provided in a therapeutically effective amount. In a specific embodiment, the compound of the present disclosure is provided in a prophylactically effective amount. In a specific embodiment, the pharmaceutical composition further contains additional therapeutic agent(s) selected from anti-cancer compounds, analgesics, antiemetics, antidepressants and anti-inflammatory agents. In a specific embodiment, the pharmaceutical composition further contains additional therapeutic agent(s) selected from different BRAF inhibitors, MEK1/2 inhibitors, PI3K inhibitors, CDK4/6 inhibitors, c-Met inhibitors, EGFR inhibitors, FGFR inhibitors, MAPK inhibitors and ERK inhibitors.

In another aspect, the present disclosure provides a method of preparing the pharmaceutical composition described above, comprising the step of: mixing the pharmaceutically acceptable excipient(s) with the compound of the present disclosure, thereby forming the pharmaceutical composition.

In another aspect, the present disclosure also provides a method of treating proliferative diseases caused by BRAF kinase mutations, comprising administering to a subject a therapeutically effective amount of the compound or the pharmaceutical composition disclosed herein. In a specific embodiment, the BRAF mutation is a V600 mutation. In a specific embodiment, the proliferative disease is melanoma characterized by a BRAF V600 mutation or colorectal cancer characterized by a BRAF V600 mutation. In a specific embodiment, the compound is administered orally, subcutaneously, intravenously or intramuscularly. In a specific embodiment, the compound is administered chronically.

Other objects and advantages of the present disclosure will be apparent to those skilled in the art from the subsequent embodiments, examples and claims.

Definitions

As used herein, unless otherwise specified, "deuterated" means that one or more hydrogens in a compound or group are substituted by deuterium; the "deuterated" may be mono-substituted, di-substituted, poly-substituted or fully-substituted by deuterium. The terms "substituted with one or more deuteriums" and "substituted one or more times by deuterium" are used interchangeably.

As used herein, unless otherwise specified, "non-deuterated compound" refers to a compound wherein the content of the deuterium atom is not higher than the natural content of the deuterium isotope (0.015%).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66.1-19. Pharmaceutically acceptable salts of the compounds disclosed herein include those derived from suitable inorganic and organic acids and inorganic and organic bases.

The compound disclosed herein may be in an amorphous or a crystalline form. In addition, the compound disclosed herein may exist in one or more crystalline forms. Therefore, the present disclosure includes all amorphous or crystalline forms of the compound disclosed herein within its scope. The term "crystal form" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

The term "crystal form" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

As used herein, the term "subject" includes, but is not limited to, humans (i.e., a male or female of any age group, e.g., a pediatric subject (e.g, infant, child, adolescent) or adult subject (e.g., young adult, middle-aged adult or elderly adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

"Disease", "disorder" and "condition" are used interchangeably herein.

As used herein, unless otherwise specified, the terms "treat", "treating", and "treatment" contemplate an action that occurs while a subject is suffering from a particular disease, disorder, or condition, which reduces the severity of the disease, disorder or condition, or retards or slows the progression of the disease, disorder or condition ("therapeutic treatment"). The terms also contemplate an action that occurs before a subject begins to suffer from a specific disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically and prophylactically effective amount.

As used herein, unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a compound of the present disclosure. For example, a compound disclosed herein may be administered simultaneously or sequentially with another therapeutic agent in separate unit dosage forms, or together with another therapeutic agent in a single unit dosage form.

DETAILED DESCRIPTION OF THE INVENTION

Compounds

In one embodiment, the present disclosure provides a compound of formula (I), or a tautomer, stereoisomer, prodrug, crystal form, pharmaceutically acceptable salt, hydrate or solvate thereof.

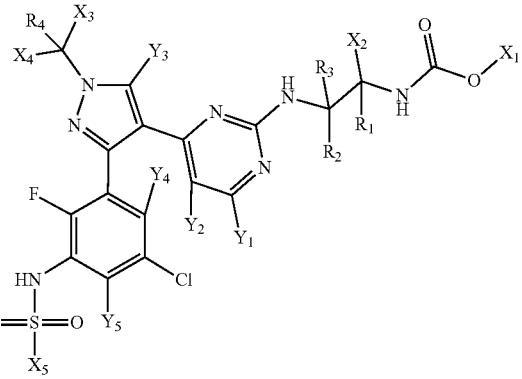

Formula (I)

wherein,
$Y_1$, $Y_2$, $Y_3$, $Y_4$ and $Y_5$ are each independently selected from hydrogen, deuterium, halogen or trifluoromethyl;
$R_1$, $R_2$, $R_3$ and $R_4$ are each independently selected from hydrogen or deuterium;
$X_1$, $X_2$, $X_3$, $X_4$ and $X_5$ are each independently selected from $CH_3$, $CD_3$, $CHD_2$ or $CH_2D$; with the proviso that the compound described above contains at least one deuterium atom.

In a specific embodiment, the content of deuterium isotope in each deuterated position is at least greater than the natural content of deuterium isotope (0.015%), alternatively greater than 30%, alternatively greater than 50%, alternatively greater than 75%, alternatively greater than 95%, or alternatively greater than 99%.

In another specific embodiment, the compound of formula (I) contains at least one deuterium atom, alternatively contains at least two deuterium atoms, alternatively contains at least three deuterium atoms, alternatively contains at least four deuterium atoms, alternatively contains at least five deuterium atoms, alternatively contains at least six deuterium atoms, alternatively contains at least seven deuterium atoms, alternatively contains at least eight deuterium atoms, alternatively contains at least nine deuterium atoms, alternatively contains at least ten deuterium atoms, alternatively contains at least eleven deuterium atoms, alternatively contains at least twelve deuterium atoms, alternatively contains at least thirteen deuterium atoms, alternatively contains at least fourteen deuterium atoms, alternatively contains at least fifteen deuterium atoms, alternatively contains at least sixteen deuterium atoms, alternatively contains at least seventeen deuterium atoms, alternatively contains at least eighteen deuterium atoms, alternatively contains at least nineteen deuterium atoms, alternatively contains at least twenty deuterium atoms, alternatively contains at least twenty-one deuterium atoms, alternatively contains at least twenty-two deuterium atoms, alternatively contains at least twenty-three deuterium atoms, or alternatively contains at least twenty-four deuterium atoms.

In another specific embodiment, "$Y_1$, $Y_2$, $Y_3$, $Y_4$ and $Y_5$ are each independently selected from hydrogen, deuterium, halogen or trifluoromethyl" includes the technical solutions wherein, $Y_1$ is selected from hydrogen, deuterium, halogen or trifluoromethyl, $Y_2$ is selected from hydrogen, deuterium, halogen or trifluoromethyl, $Y_3$ is selected from hydrogen, deuterium, halogen or trifluoromethyl, and so on, until $Y_5$ is selected from hydrogen, deuterium, halogen or trifluoromethyl. More specifically, the technical solutions wherein, $Y_1$ is hydrogen, $Y_1$ is deuterium, $Y_1$ is halogen (F, Cl, Br or I), or $Y_1$ is trifluoromethyl, $Y_2$ is hydrogen, $Y_2$ is deuterium, $Y_2$ is halogen (F, Cl, Br or I), or $Y_2$ is trifluoromethyl, $Y_3$ is hydrogen, $Y_3$ is deuterium, $Y_3$ is halogen (F, Cl, Br or I), or Y is trifluoromethyl, and so on, until $Y_5$ is hydrogen, $Y_5$ is deuterium, $Y_5$ is halogen (F, Cl, Br or I), or $Y_5$ is trifluoromethyl, are included.

In another specific embodiment, "$R_1$, $R_2$, $R_3$ and $R_4$ are each independently selected from hydrogen or deuterium" includes the technical solutions wherein, $R_1$ is selected from hydrogen or deuterium, $R_2$ is selected from hydrogen or deuterium, $R_3$ is selected from hydrogen or deuterium, and $R_4$ is selected from hydrogen or deuterium, More specifically, the technical solutions wherein, $R_1$ is hydrogen or $R_1$ is deuterium, $R_2$ is hydrogen or $R_2$ is deuterium, $R_3$ is hydrogen or $R_3$ is deuterium, and $R_4$ is hydrogen or $R_4$ is deuterium, are included.

In another specific embodiment, "$X_1$, $X_2$, $X_3$, $X_4$ and $X_5$ are each independently selected from $CH_3$, $CD_3$, $CHD_2$ or $CH_2D$" includes the technical solutions wherein, $X_1$ is selected from $CH_3$, $CD_3$, $CHD_2$ or $CH_3D$, $X_2$ is selected from $CH_3$, $CD_3$, $CHD_2$ or $CH_2D$, $X_3$ is selected from $CH_3$, $CD_3$, $CHD_2$ or $CH_2D$. and so on, until $X_5$ is selected from ($CH_3$, $CD_3$, $CHD_2$ or $CH_2D$. More specifically, the technical solutions wherein, $X_1$ is $CH_3$, $X_1$ is $CD_3$, $X_1$ is $CHD_2$ or $X_1$ is $CH_2D$, $X_2$ is $CD_3$, $X_2$ is $CD_3$, $X_2$ is $CHD_2$ or $X_2$ is $CH_2D$, $X_3$ is $CH_3$, $X_3$ is $CD_3$, $X_3$ is $CHD_2$ or $X_3$ is $CH_2D$, and so on, until $X_5$ is $CH_3$, X is $CD_3$, $X_5$ is $CHD_2$ or $X_5$ is $CH_2D$, are included.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each independently selected from hydrogen or deuterium, $R_1$ to $R_4$, and $X_1$ to $X_5$ are as defined above, with the proviso that the compound contains at least one deuterium atom.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, and $R_1$ to $R_4$, and $X_1$ to $X_5$ are as defined above, with the proviso that the compound contains at least one deuterium atom.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, $R_1$ to $R_4$ are each independently selected from hydrogen or deuterium, and $X_1$ to $X_5$ are each independently selected from $CH_3$ or $CD_3$, with the proviso that the compound contains at least one deuterium atom.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, $X_1$ is $CD_3$, $X_2$ to $X_5$ are each independently selected from $CH_3$ or $CD_3$, and $R_1$ to $R_4$ are each independently selected from hydrogen or deuterium.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, $X_2$ is $CD_3$, $X_1$, and $X_3$ to $X_5$ are each independently selected from $CH_3$ or $CD_3$, and $R_1$ to $R_4$ are each independently selected from hydrogen or deuterium.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, $X_3$ is $CD_3$, $X_1$, $X_2$, $X_4$ and $X_5$ are each independently selected from $CH_3$ or $CD_3$, and $R_1$ to $R_4$ are each independently selected from hydrogen or deuterium.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, $X_4$ is $CD_3$, $X_1$ to $X_3$ and $X_5$ are each independently selected from $CH_3$ or $CD_3$, and $R_1$ to $R_4$ are each independently selected from hydrogen or deuterium.

In another specific embodiment, the present disclosure provides a compound of formula (I), or a tautomer, stereoisomer, prodrug, crystal form, pharmaceutically acceptable salt, hydrate or solvate thereof, wherein, $Y_1$ to $Y_5$ are each hydrogen, $X_4$ is $CD_3$, $X_1$ to $X_4$ are each independently selected from $CH_3$ or $CD_3$, and $R_1$ to $R_4$ are each independently selected from hydrogen or deuterium.

In another specific embodiment, $R_1$ is deuterium; in another specific embodiment, $R_1$ is hydrogen.

In another specific embodiment, $R_2$ is deuterium; in another specific embodiment. $R_2$ is hydrogen.

In another specific embodiment, $R_3$ is deuterium, in another specific embodiment, $R_3$ is hydrogen.

In another specific embodiment, $R_2$ and $R_3$ are deuterium; in another specific embodiment, $R_2$ and $R_3$ are each hydrogen.

In another specific embodiment, $R_4$ is deuterium; in another specific embodiment. $R_4$ is hydrogen.

In another specific embodiment, $X_1$ is $CH_3$; in another specific embodiment, $X_1$ is $CD_3$.

In another specific embodiment, $X_2$ is $CH_3$; in another specific embodiment, $X_2$ is $CD_3$.

In another specific embodiment, $X_3$ is $CH_3$; in another specific embodiment, $X_3$ is $CD_3$.

In another specific embodiment, $X_4$ is $CH_3$; in another specific embodiment, $X_4$ is $CD_3$.

In another specific embodiment, $X_5$ is $CH_3$; in another specific embodiment, $X_5$ is $CD_3$.

In another specific embodiment, $R_2$ and $R_3$ are deuterium, and $X_2$ is $CD_3$; in another specific embodiment, $R_2$ and $R_3$ are each hydrogen, and $X_2$ is $CH_3$.

In another specific embodiment, $R_4$ is deuterium, and $X_3$ and $X_4$ are each $CD_3$; in another specific embodiment, $R_4$ is hydrogen, and $X_3$ and $X_4$ are each $CH_3$.

In another embodiment, the present disclosure provides a compound of formula (Ia):

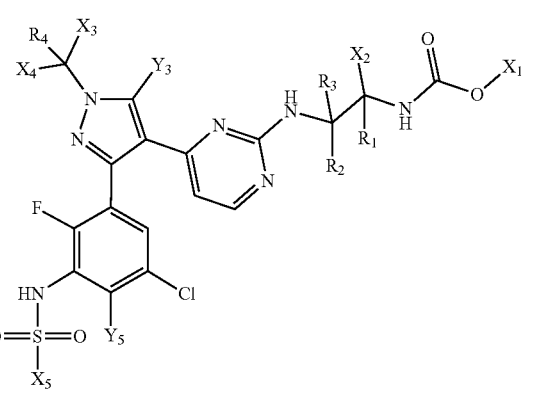

wherein, $R_1$, $R_2$, $R_3$ and $R_4$ are each independently selected from hydrogen or deuterium;

$X_1$, $X_2$, $X_3$, $X_4$ and $X_5$ are each independently selected from $CH_3$, $CD_3$, $CHD_2$ or $CH_2D$;

with the proviso that the compound described above contains at least one deuterium atom; or a tautomer, stereoisomer, prodrug, crystal form, pharmaceutically acceptable salt, hydrate or solvate thereof.

In another embodiment, the present disclosure provides a compound of formula (II) or (III):

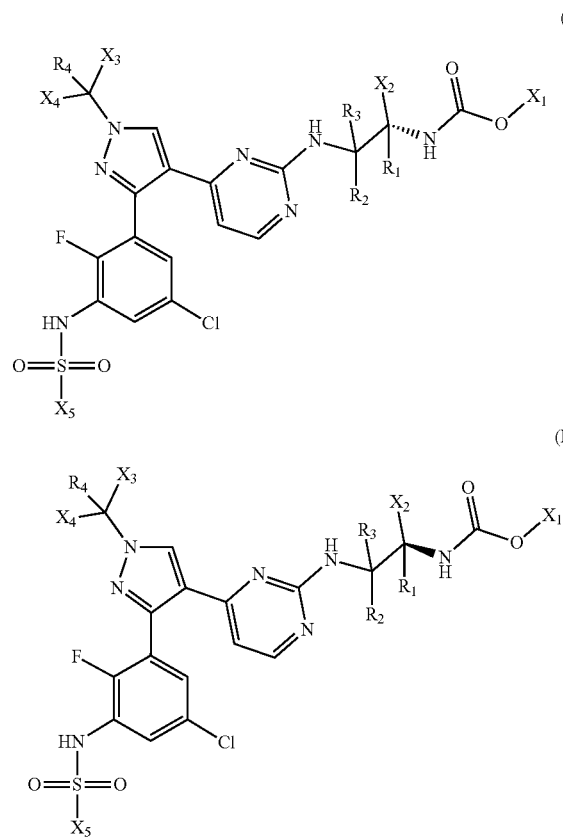

wherein, $R_1$, $R_2$, $R_3$ and $R_4$ are each independently selected from hydrogen or deuterium;

$X_1$, $X_2$, $X_3$, $X_4$ and $X_5$ are each independently selected from $CH_3$, $CD_3$, $CHD_2$ or $CH_2D$;

with the proviso that the compound described above contains at least one deuterium atom; or a tautomer, stereoisomer, prodrug, crystal form, pharmaceutically acceptable salt, hydrate or solvate thereof.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_5$ is $CH_3$, $R_1$ to $R_4$ are each independently selected from hydrogen or deuterium, and $X_1$ to $X_4$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ is hydrogen, $R_2$ to $R_4$ are each independently selected from hydrogen or deuterium, and $X_1$ to $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ is hydrogen, $R_2$ to $R_4$ are each independently selected from hydrogen or deuterium, and $X_1$ to $X_5$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ is hydrogen, $X_5$ is $CH_3$, $R_2$ to $R_4$ are each independently selected from hydrogen or deuterium, and $X_1$ to $X_4$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ is hydrogen, $X_5$ is $CH_3$, $R_2$ to $R_4$ are each independently selected from hydrogen or deuterium, and $X_1$ to $X_4$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ and $R_3$ are each hydrogen, $X_2$ is $CH_3$, $R_1$ and $R_4$ are each independently selected from hydrogen or deuterium, and $X_1$ and $X_3$ to $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ and $R_3$ are each hydrogen, $X_2$ is $CH_3$, $R_1$ and $R_4$ are each independently selected from hydrogen or deuterium, and $X_1$ and $X_3$ to $X_5$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ and $R_3$ are each hydrogen, $X_2$ and $X_5$ are each $CH_3$, $R_1$ and $R_4$ are each independently selected from hydrogen or deuterium, and $X_1$, $X_3$ and $X_4$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ and $R_3$ are each hydrogen, $X_2$ and $X_5$ are each $CH_3$, $R_1$ and $R_4$ are each independently selected from hydrogen or deuterium, and $X_1$, $X_3$ and $X_4$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_3$ are each hydrogen, $X_2$ is $CH_3$, $R_4$ is selected from hydrogen or deuterium, $X_1$ and $X_3$ to $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_3$ are each hydrogen, $X_2$ is $CH_3$, $R_4$ is selected from hydrogen or deuterium, and $X_1$ and $X_3$ to $X_5$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_3$ are each hydrogen, $X_2$ and $X_5$ are each $CH_3$, $R_4$ is selected from hydrogen or deuterium, and $X_1$, $X_3$ and $X_4$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_3$ are each hydrogen, $X_2$ and $X_5$ are each $CH_3$, $R_4$ is selected from hydrogen or deuterium, and $X_1$, $X_3$ and $X_4$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_4$ is hydrogen, $X_3$ and $X_4$ are each $CH_3$, $R_1$ to $R_3$ are each independently selected from hydrogen or deuterium, and $X_1$, $X_2$ and $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_4$ is hydrogen, $X_3$ and $X_4$ are each $CH_3$, $R_1$ to $R_3$ are each independently selected from hydrogen or deuterium, and $X_1$, $X_2$ and $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_4$ is hydrogen, $X_3$ to $X_5$ are each $CH_3$, $R_1$ to $R_3$ are each independently selected from hydrogen or deuterium, and $X_1$ and $X_2$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_4$ is hydrogen, $X_3$ to $X_5$ are each $CH_3$, $R_1$ to $R_3$ are each independently selected from hydrogen or deuterium, and $X_1$ and $X_2$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ and $R_4$ are each hydrogen, $X_3$ and $X_4$ are each $CH_3$, $R_2$ and $R_3$ are each independently selected from hydrogen or deuterium, and $X_1$, $X_2$ and $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ and $R_4$ are each hydrogen, $X_3$ and $X_4$ are each $CH_3$, $R_2$ and $R_3$ are each independently selected from hydrogen or deuterium, and $X_1$, $X_2$ and $X_5$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ and $R_4$ are each hydrogen, $X_3$ to $X_5$ are each $CH_3$, $R_2$ and $R_3$ are each independently selected from hydrogen or deuterium, and $X_1$ and $X_2$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ and $R_4$ are each hydrogen, $X_3$ to $X_5$ are each $CH_3$, $R_2$ and $R_3$ are each independently selected from hydrogen or deuterium, and $X_1$ and $X_3$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ to $R_4$ are each hydrogen, $X_2$ to $X_4$ are each $CH_3$, $R_1$ is selected from hydrogen or deuterium, and $X_1$ and $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ to $R_4$ are each hydrogen, $X_2$ to $X_4$ are each $CH_3$, $R_1$ is selected from hydrogen or deuterium, and $X_1$ and $X_5$ are each independently selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ to $R_4$ are each hydrogen, $X_2$ to $X_5$ are each $CH_3$, $R_1$ is selected from hydrogen or deuterium, and $X_1$ is selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_2$ to $R_4$ are each hydrogen, $X_2$ to $X_5$ are each $CH_3$, $R_1$ is selected from hydrogen or deuterium, and $X_1$ is selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_4$ are each hydrogen, $X_2$ to $X_4$ are each $CH_3$, and $X_1$ and $X_5$ are each independently selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_4$ are each hydrogen, $X_2$ to $X_4$ are each $CH_3$, and $X_1$ and $X_5$ are each independently selected from $CH_3$ or $CD_3$, with the proviso that the compound described above contains at least one deuterium atom.

In another specific embodiment, the present disclosure provides a compound of formula (Ia), formula (II) or formula (III) or a tautomer, stereoisomer, prodrug, crystal form, pharmaceutically acceptable salt, hydrate or solvate thereof, herein, $R_1$ to $R_4$ are each hydrogen, $X_2$ to $X_5$ are each $CH_3$, and $X_1$ is selected from $CH_3$, $CD_3$, $CHD_2$ or $CH_2D$, with the proviso that the compound described above contains at least one deuterium atom. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $R_1$ to $R_4$ are each hydrogen, $X_2$ to $X_5$ are each $CH_3$, and $X_1$ is selected from $CH_3$ or $CD_3$, with the proviso that the compound described above contains at least one deuterium atom.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $R_1$ to $R_4$ are each independently selected from hydrogen or deuterium, and $X_2$ to $X_5$ are each independently selected from $CH_3$, $CD_3$, $CHD_3$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $R_1$ to $R_4$ are each independently selected from hydrogen or deuterium, and $X_2$ to $X_5$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_5$ is $CH_3$, $R_1$ to $R_4$ are each independently selected from hydrogen or deuterium, and $X_2$ to $X_4$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_5$ is $CH_3$, $R_1$ to $R_4$ are each independently selected from hydrogen or deuterium, and $X_2$ to $X_4$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $R_1$ is hydrogen, $R_2$ to $R_4$ are each independently selected from hydrogen or deuterium, and $X_2$ to $X_5$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $R_1$ is hydrogen, $R_2$ to $R_4$ are each independently selected from hydrogen or deuterium, and $X_2$ to $X_5$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_5$ is $CH_3$, $R_1$ is hydrogen, $R_2$ to $R_4$ are each independently selected from hydrogen or deuterium, and $X_2$ to $X_4$ are each independently selected from $CH_3$, $CD_3$, $CHD_2$ or $CH_2D$. In another specific embodiment, the present disclosure provides a compound of formula (Ia), formula (TT) or formula (III), or a tautomer, stereoisnmer, prodrug, crystal form, pharmaceutically acceptable salt, hydrate or solvate thereof, wherein, $X_1$ is $CD_3$, $X_5$ is $CH_3$, $R_2$ is hydrogen, $R_2$ to $R_4$ are each independently selected from hydrogen or deuterium, and $X_2$ to $X_4$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ is $CH_3$, $R_2$ and $R_3$ are each hydrogen, $R_1$ and $R_4$ are each independently selected from hydrogen or deuterium, and $X_3$ to $X_5$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ is $CH_3$, $R_2$ and $R_3$ are each hydrogen, $R_1$ and $R_4$ are each independently selected from hydrogen or deuterium, and $X_3$ to $X_5$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ and $X_5$ are each $CH_3$, $R_2$ and $R_3$ are each hydrogen, $R_1$ and $R_4$ are each independently selected from hydrogen or deuterium, and $X_3$ and $X_4$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ and $X_5$ are each $CH_3$, $R_2$ and $R_3$ are each hydrogen, $R_1$ and $R_4$ are each independently selected from hydrogen or deuterium, and $X_3$ and $X_4$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ is $CH_3$, $R_1$ to $R_3$ are each hydrogen, $R_4$ is selected from hydrogen or deuterium, and $X_3$ to $X_5$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ is $CH_3$, $R_1$ to $R_3$ are each hydrogen, $R_4$ is selected from hydrogen or deuterium, and $X_3$ to $X_5$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ and $X_5$ are each $CH_3$, $R_1$ to $R_3$ are each hydrogen, $R_4$ is selected from hydrogen or deuterium, and $X_3$ and $X_4$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ and $X_5$ are each $CH_3$, $R_1$ to $R_3$ are each hydrogen, $R_4$ is selected from hydrogen or deuterium, and $X_3$ and $X_4$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ and $X_4$ are each $CH_3$, $R_4$ is hydrogen, $R_1$ to $R_3$ are each independently selected from hydrogen or deuterium, and $X_2$ and $X_5$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ and $X_4$ are each $CH_3$, $R_4$ is hydrogen, $R_1$ to $R_3$ are each independently selected from hydrogen or deuterium, and $X_2$ and $X_5$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ to $X_5$ are each $CH_3$, $R_4$ is hydrogen, $R_1$ to $R_3$ are each independently selected from hydrogen or deuterium, and $X_2$ is selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ to $X_5$ are each $CH_3$, $R_4$ is hydrogen, $R_1$ to $R_3$ are each independently selected from hydrogen or deuterium, and $X_2$ is selected from $CH_3$, or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ and $X_4$ are each $CH_3$, $R_1$ and $R_4$ are each hydrogen, $R_2$ and $R_3$ are each independently selected from hydrogen or deuterium, and $X_2$ and $X_5$ are each independently selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ and $X_4$ are each $CH_3$, $R_1$ and $R_4$ are each hydrogen, $R_2$ and $R_3$ are each independently selected from hydrogen or deuterium, and $X_2$ and $X_5$ are each independently selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ to $X_5$ are each $CH_3$, $R_1$ and $R_4$ are each hydrogen, $R_2$ and $R_3$ are each independently selected from hydrogen or deuterium, and $X_2$ is selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_3$ to $X_5$ are each $CH_3$, $R_1$ and $R_4$ are each hydrogen, $R_2$ and $R_3$ are each independently selected from hydrogen or deuterium, and $X_2$ is selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ to $X_4$ are each $CH_3$, $R_2$ to $R_4$ are each hydrogen, $R_1$ is selected from hydrogen or deuterium, and $X_5$ is selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ to $X_4$ are each $CH_3$, $R_2$ to $R_4$ are each hydrogen, $R_1$ is selected from hydrogen or deuterium, and $X_5$ is selected from $CH_3$ or $CD_3$.

In another specific embodiment, the present disclosure provides a compound of formula (Ia), formula (TI) or formula (III), or a tautomer, stereoisomer, prodrug, crystal form, pharmaceutically acceptable salt, hydrate or solvate thereof, wherein, $X_1$ is $CD_3$, $X_2$ to $X_5$ are each $CH_3$, $R_2$ to $R_4$ are each hydrogen, and $R_1$ is selected from hydrogen or deuterium.

In another specific embodiment, the present disclosure provides a compound of formula (Ia), formula (II) or formula (III) or a tautomer, stereoisomer, prodrug, crystal form, pharmaceutically acceptable salt, hydrate or solvate thereof, wherein, $X_1$ is $CD_3$, $X_2$ to $X_4$ are each $CH_3$, $R_1$ to $R_4$ are each hydrogen, and $X_4$ is selected from $CH_3$, $CD_3$, $CHD_2$ or $CH_2D$. In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ to $X_4$ are each $CH_3$, $R_1$ to $R_4$ are each hydrogen, and $X_5$ is selected from $CH_3$ or $CD_3$.

In another specific embodiment, the present disclosure provides a compound of formula (Ia), formula (II) or formula (III), or a tautomer, stereoisomer, prodrug, crystal form, pharmaceutically acceptable salt, hydrate or solvate thereof, wherein, $X_1$ is $CD_3$, $X_2$ to $X_5$ are each $CH_3$, and $R_1$ to $R_4$ are each hydrogen.

As an alternative specific embodiment, the compound is represented by any of the following structures, or a pharmaceutically acceptable salt thereof, but is not limited to the following structures:

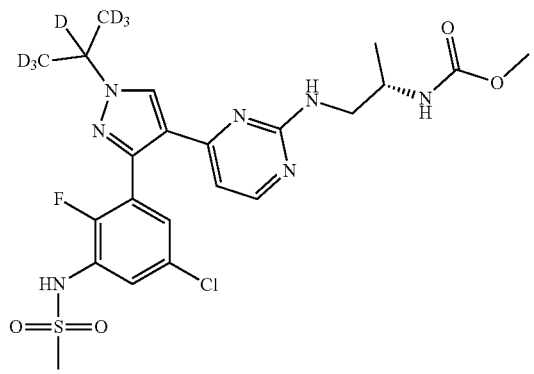

,

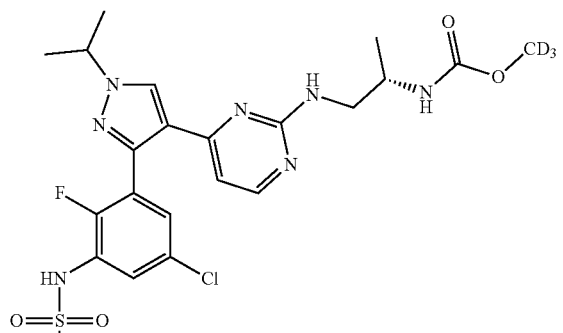

,

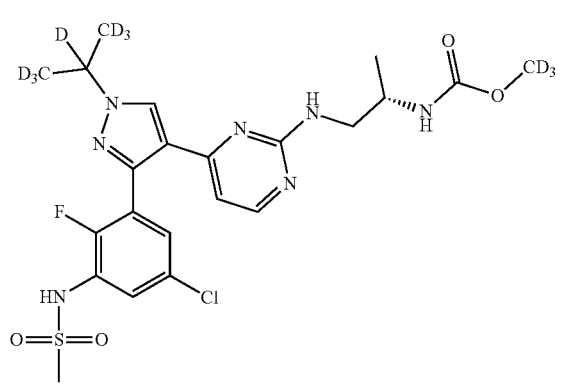

,

-continued

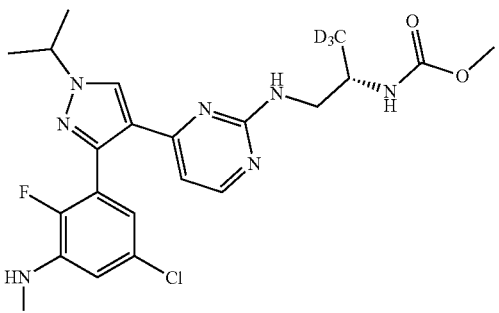

,

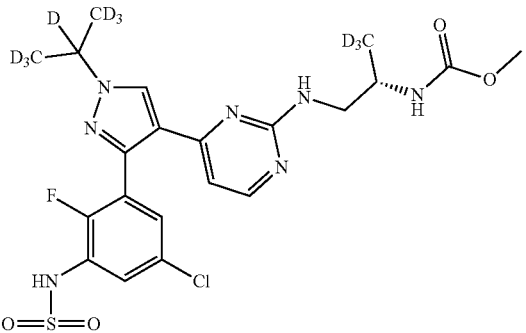

,

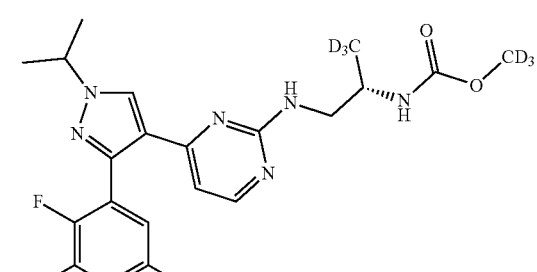

,

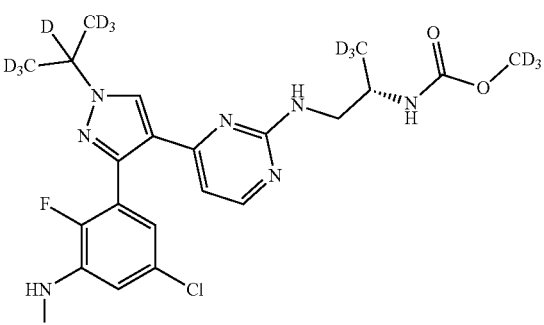

,

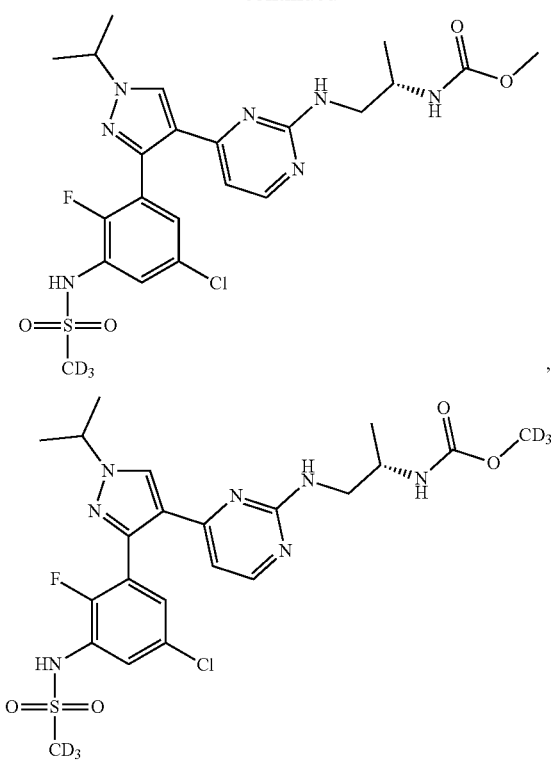
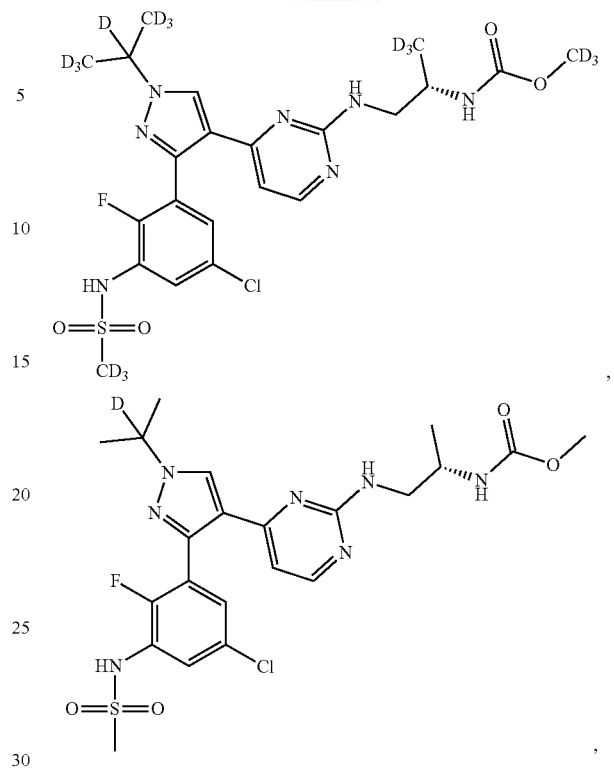
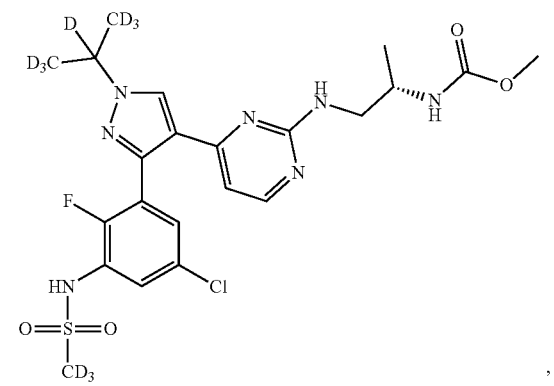
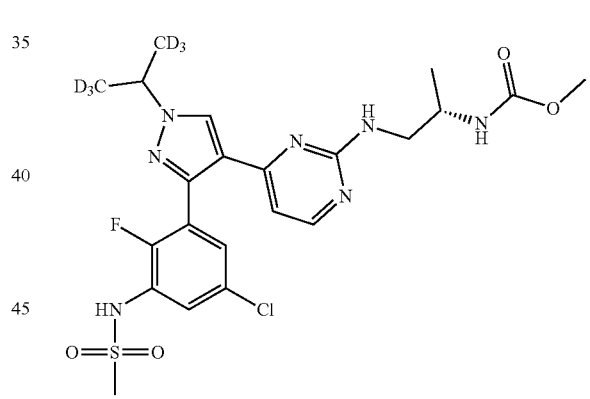
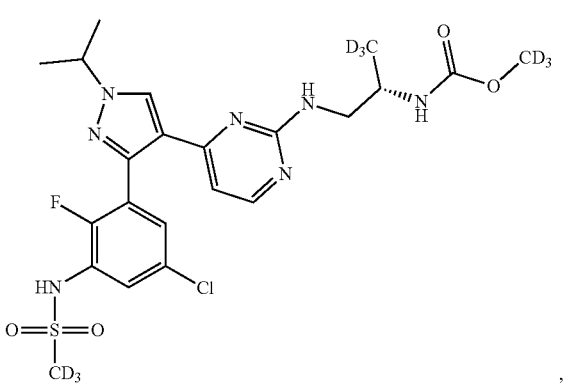
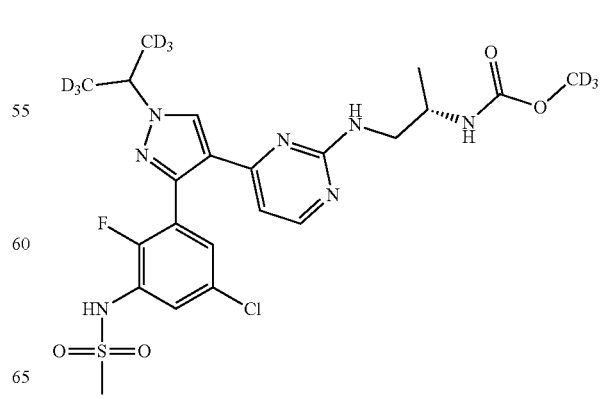

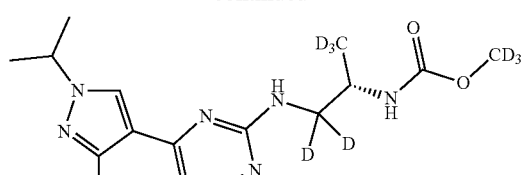
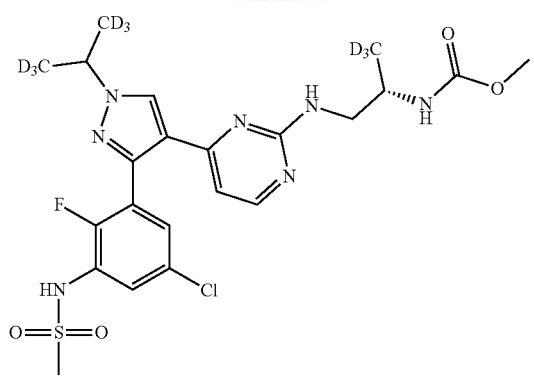
,
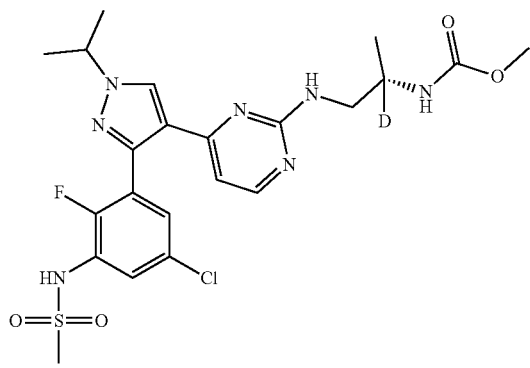
,
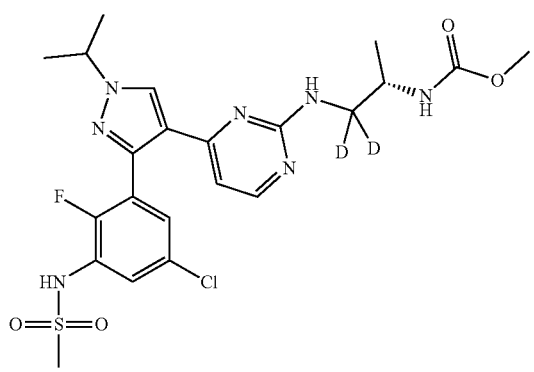
,
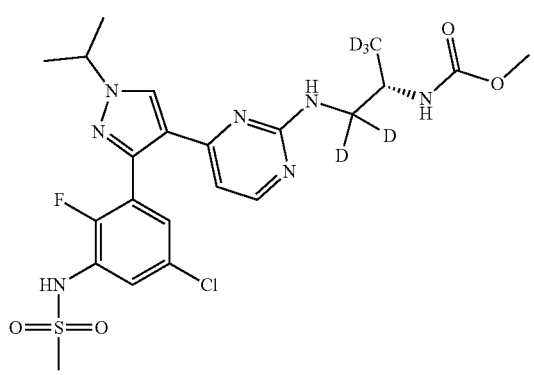
,
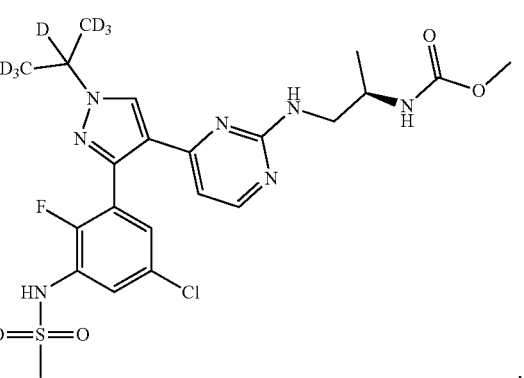
,
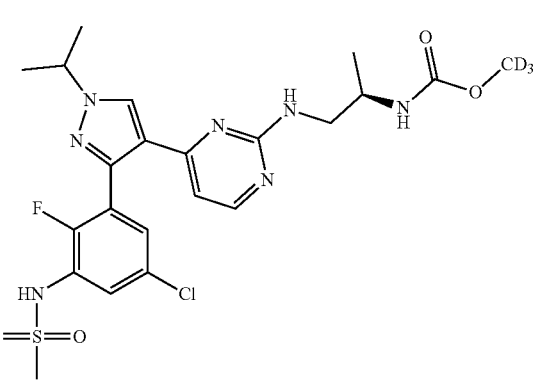
,

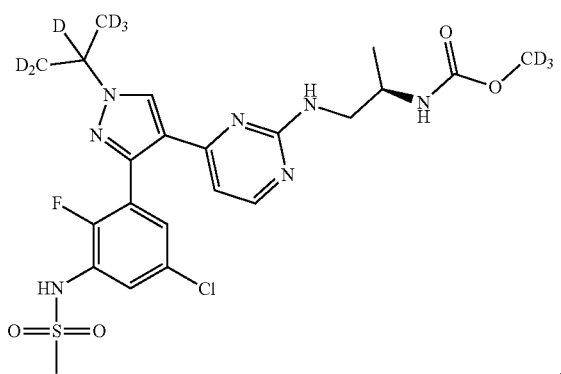
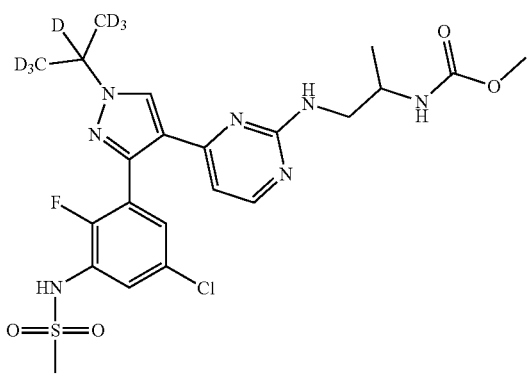
,
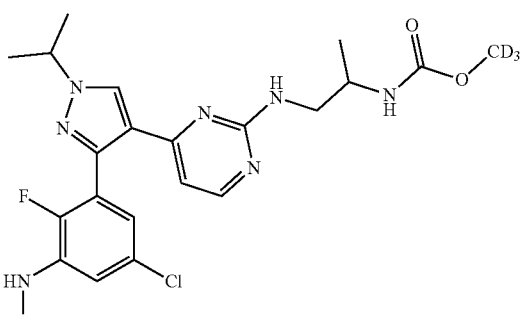
,
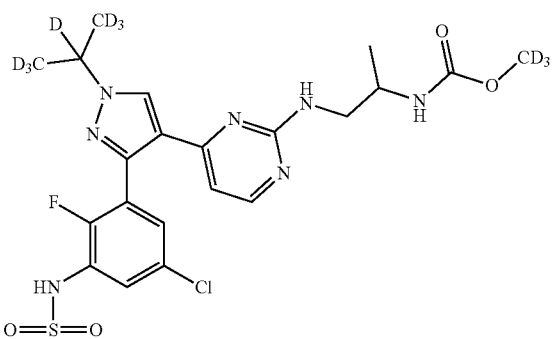
,
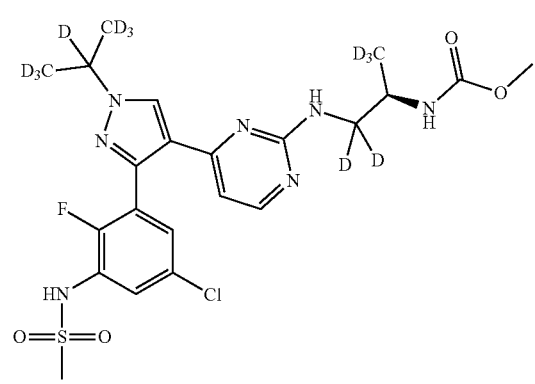
,

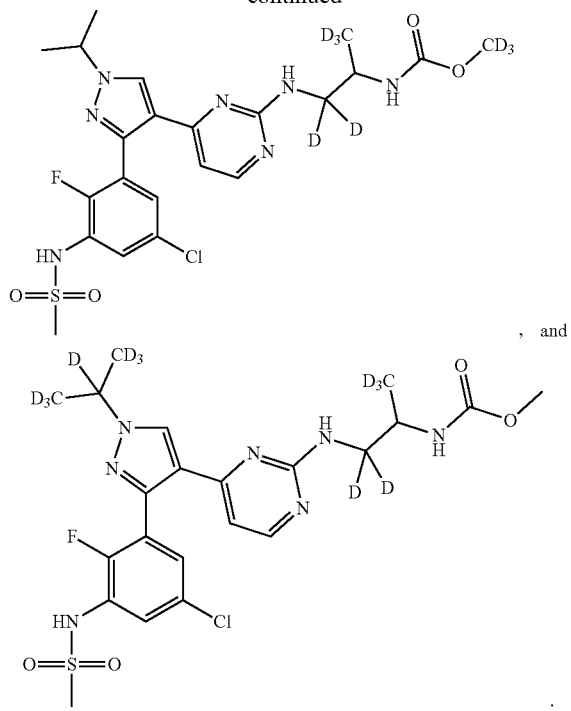

, and

The compound disclosed herein may include one or more asymmetric centers, and thus may exist in a variety of "stereoisomeric" forms, for example, enantiomeric and/or diastereomeric forms. For example, the compound disclosed herein may be in the form of an individual enantiomer, a diastereomer or a geometric isomer (e.g., cis- and trans-isomers), or may be in the form of a mixture of stereoisomers, including a racemic mixture and a mixture enriched in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

Those skilled in the art will appreciate that organic compounds can form complexes with solvents that react in or precipitate or crystallize from the solvent. These complexes are referred to as "solvates." When the solvent is water, the complex is referred to as a "hydrate." The invention encompasses all solvates of the compounds disclosed herein.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula $R \cdot x\ H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates ($R \cdot 0.5\ H_2O$)) and polyhydrates (x is a number greater than 1, for example, dihydrates ($R \cdot 2H_2O$) and hexahydrates ($R \cdot 6H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

Also disclosed herein are isotopically labeled compounds, which are equivalent to those described in formula (I), but one or more atoms are replaced by atoms having an atom mass or mass number that are different from that of atoms that are common in nature, Examples of isotopes that can be listed in compounds disclosed herein include hydrogen, carbon, nitrogen, oxygen, phosphorus, sulfur, fluorine and chlorine isotopes, such as $^2H$, $^3H$, $^3C$, $^{11}C$, $^{14}C$, $^{15}N$, $^{18}O$, $^{17}O$, $^{31}P$, $^{32}P$, $^{35}P$, $^{35}S$, $^8F$ and $^{36}Cl$, respectively. A compound disclosed herein containing the above isotope and/or other isotope of other atoms, a prodrug thereof, or a pharmaceutically acceptable salt of said compound or prodrug are all within the scope disclosed herein. Certain isotopically labeled compounds disclosed herein, such as those incorporating radioisotopes (e.g., $^3H$ and $^{14}C$, can be used in the tissue distribution experiments of drugs and/or substrates. Tritium, i.e., $^3H$, and carbon-14, i.e., $^{14}C$, are particularly preferred, because they are easier to be prepared and detected. In addition, substitution with heavier isotopes such as deuterium, i.e., $^2H$, may provide therapeutic benefits due to the higher metabolic stability, for example, increased half-life in vivo or reduced dosage, and thus priority may be given in some cases. Isotopically-labeled compounds of formula (I) disclosed herein and prodrugs thereof can be prepared using the following schemes and/or the procedures disclosed in the examples and preparation examples by replacing the non-isotopic reagents with readily available isotopically labeled reagents.

In addition, a prodrug is also included within the context disclosed herein. The term "prodrug" as used herein refers to a compound, which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each of which is incorporated herein by reference.

A prodrug is any covalently bonded compound disclosed herein which, when administered to a patient, releases the parent compound in vivo. A prodrug is typically prepared by modifying a functional group in such a way that the modification can be cleaved either by routine manipulation or decompose in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, the acetate/acetamide, formate/formamide and benzoate/benzamide derivatives of the hydroxyl, mercapto and amino functional groups of the compound of formula (I). Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those, which readily decompose in a human body to release a parent acid or its salt.

Pharmaceutical Compositions, Formulations and Kits

In another aspect, provided herein is a pharmaceutical composition comprising the compound disclosed herein (also referred to as "active component") and pharmaceutically acceptable excipient(s). In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The "pharmaceutically acceptable excipient" for use in the present disclosure refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g. human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The present disclosure also includes a kit (e.g., pharmaceutical packs). The kit provided may include compounds disclosed herein, other therapeutic agents, and first and second containers containing the compounds disclosed herein and other therapeutic agents (e.g., vials, ampoules, bottles, syringes, and/or dispersible packages or other suitable containers). In some embodiments, the kit provided can also optionally include a third container containing a pharmaceutically acceptable excipient for diluting or suspending compounds disclosed herein and/or other therapeutic agents. In some embodiments, the compounds disclosed herein and other therapeutic agents provided in a first container and a second container are combined to form a unit dosage form.

The pharmaceutical composition provided herein can be administered by a variety of routes including, but not limited to, oral administration, parenteral administration, inhalation administration, topical administration, rectal administration, nasal administration, buccal cavity administration, vaginal administration, administration by implant or other means of administration. For example, the parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the condition disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to the administration of a compound or pharmaceutical composition thereof over an extended period of time, for example, over 3 months, 6 months, 1 year, 2 years, 3 years, 5 years, etc, or may be continued indefinitely, for example, for the rest of the subject's life. In some embodiments, the chronic administration is intended to provide a constant level of the compound in the blood, e.g., within the therapeutic window over the extended period of time.

The pharmaceutical compostions disclosed herein may be further delivered using a variety of dosing methods. For example, in some embodiments, the pharmaceutical composition may be given as a bolus, e.g., in order to rapidly raise the concentration of the compound in the blood to an effective level. The placement of the bolus dose depends on the systemic levels of the active ingredient desired, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g, by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1% to about 50% by weight or alternatively from about 1% to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 mg/kg to about 20 mg/kg of the compound disclosed herein, with preferred doses each providing from about 0.1 mg/kg to about 10 mg/kg, and especially about 1 mg/kg to about 5 mg/kg.

Transdermal doses are generally selected to provide similar or lower blood levels than are achieved using injection doses, generally in an amount ranging from about 0.01% to about 20% by weight, alternatively from about 0.1% to about 20% by weight, alternatively from about 0.1% to about 10% by weight, or yet alternatively from about 0.5% to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As mentioned before, the active compound in such compositions is typically a minor component, often being from about 0.05% to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the stable dermal penetration of the active ingredients or formulation. All such known transdermal formulations and ingredients are included within the scope provided herein.

The compounds disclosed herein can also be administered by a transdermal device. Accordingly, transdermal administration can be accomplished using a reservoir or a patch in porous membrane type or with various solid matrixes.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds disclosed herein can also be administered in sustained release forms or from sustained release drug delivery systems. A description of representative sustained release materials can be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are ($\alpha$-, $\beta$- and $\gamma$-cyclodextrins consisting of 6, 7 and 8 $\alpha$-1,4-linked glucose units, respectively, optionally comprising one or more substituents on the linked sugar moieties, which include, but are not limited to, methylated, hydroxyalkylated, acylated, and sulfoalkylether substitution. In some embodiments, the cyclodextrin is a sulfoalkyl ether $\beta$-cyclodextrin, e.g., sulfobutyl ether $\beta$-cyclodextrin, also known as Captisol. See, e.g., U.S. 5,376,645. In some embodiments, the formulation comprises hexapropyl-$\beta$-cyclodextrin (e.g., 10% to 50% in water).

Indications

The compounds of the present disclosure are capable of regulating kinase activity and can therefore be used in the treatment of diseases and disorders in which kinases play a role in the pathology and/or symptomology of the diseases. Examples of kinases inhibited by the compounds and compositions disclosed herein and the methods used include, but are not limited to, B-Raf, including mutant forms of B-Raf.

In an alternative embodiment, the present disclosure relates to a method of treating proliferative diseases characterized by BRAF kinase mutations. The method comprises administering a BRAF inhibitor through a dosing regimen to inhibit the resistance to BRAE Inhibitor treatment.

Alternatively, the BRAF mutation in this method is a V600 mutation, such as BRAF V600E.

Alternatively, the proliferative diseases in this method include cancer, such as, but not limited to, bladder cancer, breast cancer, brain cancer, head and neck cancer, liver cancer, biliary tract cancer, acute and chronic lymphocytic leukemia, acute and chronic myeloid leukemia, chronic myelomonocytic leukemia, colorectal cancer, gastric cancer, gastrointestinal stromal tumor, glioma, lymphoma, melanoma, multiple myeloma, myeloproliferative and extramedullary proliferative disease, neuroendocrine cancer, lung cancer, pancreatic cancer, ovarian cancer, prostate cancer, renal cell carcinoma, sarcoma and thyroid cancer, such as papillary thyroid cancer. Other proliferative diseases include mast cell leukemia, germ cell tumor, small cell lung cancer, gastrointestinal stromal tumor, neuroblastoma, and osteosarcoma.

Yet alternatively, the proliferative disease treated by the compound disclosed herein is melanoma characterized by a V600 mutation (such as BRAF V600E), or colorectal cancer characterized by a V600 mutation (such as BRAF V600E).

Combination Therapy

The compound disclosed herein can be administered in a therapeutically effective amount in combination with one or more therapeutic agents (pharmaceutical combinations). For example, it may have a coordinated effect with other anti-tumor agents or anti-proliferative agents, such as mitotic inhibitors, alkylating agents, antimetabolites, inserted antibiotics, growth factor inhibitors, cell cycle inhibitors, enzymes, topoisomerase inhibitors, biological response modifiers, antibodies, cytotoxic drugs, anti-hormones, anti-androgens, anti-angiogenic agents, kinase inhibitors, pan-kinase inhibitors or growth factor inhibitors.

In one embodiment of the present disclosure, the additional therapeutic agents are selected from anticancer drugs, analgesics, antiemetics, antidepressants or anti-inflammatory drugs. In addition, the additional therapeutic agents are different BRAF inhibitors. MEK1/2 inhibitors, PI3K inhibitors, CDK4/6 inhibitors, c-Met inhibitors, EGFR inhibitors, FGFR inhibitors, MAPK inhibitors or ERK inhibitors, and are administered individually in combination with the compound disclosed herein. For example, the addition of a MEK1/2 inhibitor in combination with a Raf inhibitor leads to the significant inhibition of ERR signal transduction, and therefore reduces cell proliferation and transformation. Since MEK1/2 inhibitor treatment alone has caused dose-limiting toxicity in clinic, the combination of Raf and MEK1/2 inhibitors is a better treatment strategy.

Examples of MEK1/2 inhibitors are AS703026 (EMD Serono); MSC1936369B (EMD Serono); GSK1120212 (GlaxoSmithKline); AZD6244 (AstraZeneca); PD-0325901 (Pfizer); ARRY-438162 (Array BioPharma); RDEA119 (Ardea Biosciences); GDC0941 (Genentech); GDC0973 (Genentech); TAK-733 (Millennium Pharma); RO5126766 (Hoffman-La Roche) and XL-518 (Exelixis).

The CDK4/6 inhibitors are known in the art and include flavopiridol, PI446A-05, LEE011, AT7519, BMS265246, LY2835219, and PD-0332991.

The PI3K inhibitors are known in the art and include perifosine, CAL-101, PX-866. BEZ235, SF1126, INK1117, GDC-0941, BKM120, XL147, XL765, Palomnid529, GSK105965, Zstk474, PTW33597, IC87114, TG100-115, CAL283, PI-103, BYL719, GNE-477, GUDC-907 and AEZS-136.

The c-Met inhibitors are known in the art and include crizotinib, PHA-665752, SU11274, PF-04217903, foretinib, SGX523, JNJ-38877605, GSK1363089, AMG208, and INCB28060.

The EGFR inhibitors are alternatively erlotinib, and monoclonal antibodies (e.g., cetuximab and panitumumab).

The FGFR inhibitors are alternatively selective and ATP-competitive pan-FGFR kinase inhibitors, including AZD4547 and BGJ398.

The present disclosure further relates to a therapeutic combination comprising the BARF inhibitor disclosed herein and a second inhibitor selected from MEK1/2 inhibitors, PI3K inhibitors, CDK4/6 inhibitors, c-Met inhibitors, EGFR inhibitors or FGFR inhibitors, for separate, simultaneous or sequential administration. More specifically, the therapeutic combination comprises the compound disclosed herein and a second inhibitor selected from MEK1/2 inhibitors, PI3K inhibitors, CDK4/6 inhibitors, c-Met inhibitors, EGFR inhibitors or FGFR inhibitors or pharmaceutically acceptable salts thereof, for separate, simultaneous or sequential administration.

The present disclosure further relates to a method of treating proliferative diseases characterized by mutations in B-Raf in a subject, which comprises administering to the subject a therapeutically effective amount of the combination comprising the compound disclosed herein and a second inhibitor alternatively selected from MEK1/2 inhibitors, PI3K inhibitors, CDK4/6 inhibitors, c-Met inhibitors, EGFR inhibitors or FGFR inhibitors. More specifically, the present disclosure relates to a method of treating proliferative diseases characterized by mutations in B-Raf (such as V600 mutations) (e.g., melanoma characterized by a BRAF V600 mutation) in a subject, which comprises administering to the subject a therapeutically effective amount of the combination disclosed herein. Alternatively, these inhibitors are administered in a therapeutically effective dose, and they provide beneficial effects when combined. The administration may be carried out separately, simultaneously or sequentially.

The present disclosure also relates to the preparation of the pharmaceutical composition or the combination of drugs disclosed herein for treating or preventing proliferative diseases in a subject in need, especially the proliferative diseases characterized by mutations in B-Raf, particularly BRAF V600 mutations (e.g., melanoma characterized by a BRAF V600 mutation).

Preparation Method of the Compound Disclosed Herein

The compounds disclosed herein, including their salts, can be prepared using known organic synthetic techniques and can be synthesized according to any of various possible synthetic routes, such as those in the schemes below. The reaction for preparing compounds disclosed herein can be carried out in a suitable solvent, which can be easily selected by those skilled in the art of organic synthesis. The suitable solvent can be substantially unreactive with starting materials (reactants), intermediates or products at the temperature at which the reaction is carried out (for example, at temperatures ranging from the freezing temperature to boiling temperature of the solvent). A given reaction can be carried out in one solvent or a mixture of more than one solvent. The skilled person can select the solvent for the particular reaction step depending on the particular reaction step.

The preparation of the compounds disclosed herein may involve protection and deprotection of different chemical groups. One skilled in the art can readily determine the need for protection and deprotection and the choice of appropriate protective groups. The chemical properties of protective groups can be found, for example, in Wuts and Greene, Protective Groups in Organic Synthesis, 4th Ed., John Wiley & Sons: New Jersey, (2006), which is incorporated herein by reference in its entirety.

The compound of the present disclosure can be prepared as an individual stereoisomer thereof by reacting a racemic mixture of the compound with an optically active resolving agent to form a pair of diastereomeric compounds, separating the diastereomers, and recovering the optically pure enantiomer. The resolution of enantiomers can be carried out using a diastereomeric derivative of the compound disclosed herein, or alternatively, the dissociable complexes (for example, crystalline diastereomeric salts). Diastereomers have significantly different physical properties (for example, melting point, boiling point, solubility, reactivity, etc.), and can be easily separated by taking advantage of these dissimilarities. Diastereomers can be separated by chromatography, or alternatively by separation/resolution techniques based on differences in solubility. The optically pure enantiomer is then recovered, along with the resolving reagent, by any practical means that would not result in racemization. A more detailed description of the techniques applicable to the resolution of a racemic mixture to obtain stereoisomers of a compound can be found in Jean Jacques, Andre Collet, Samuel H. Wilen, "Enantiomers, Racemates and Resolutions", John Wiley And Sons, Inc., 1981.

The reaction can be monitored according to any suitable method known in the art. For example, product formation can be monitored by spectroscopic means (such as nuclear magnetic resonance (NMR) spectroscopy (e.g., $^1$H or $^{13}$C), infrared (IR) spectroscopy, spectrophotometry (e.g., UV-visible), mass spectrometry (MS)) or by chromatographic methods (such as high performance liquid chromatography (HPLC) or thin layer chromatography (TLC)).

The compound of formula (I) of the present disclosure can be prepared as shown in the following reaction scheme 1:

Reaction scheme 1

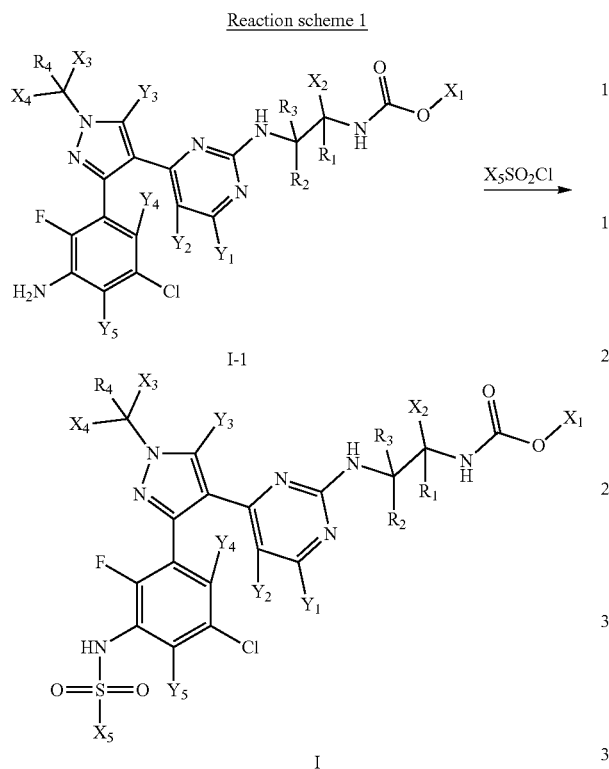

wherein $Y_1$, $Y_2$, $Y_3$, $Y_4$, $Y_5$, $R_1$, $R_2$, $R_3$, $R_4$, $X_1$, $X_2$, $X_3$, $X_4$ and $X_5$ are as defined in the summary of the invention. The compound of formula (I) may be prepared by the reaction of the compound of formula (I-1) with the sulfonating reagent $X_5SO_2Cl$ in the presence of a suitable alkali (e.g., pyridine, triethylamine, 4-(N,N-dimethylamino)pyridine, etc.) and a suitable solvent (e.g., dichloromethane, THF, etc.). The reaction is carried out at a temperature ranging from about 0° C. to about 1000° C., and may take up to about 20 hours to complete. The reaction mixture is optionally further reacted to remove any protective groups.

The compound of formula (I-1) can be prepared by the following reaction scheme 2:

Reaction scheme 2

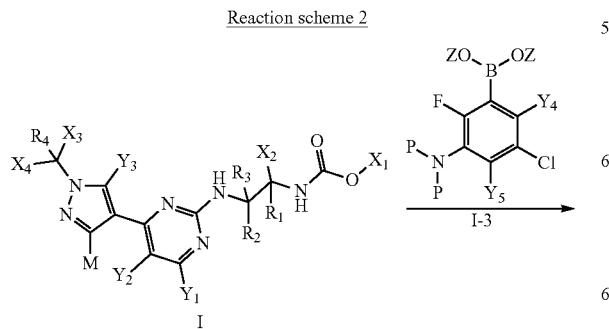

-continued

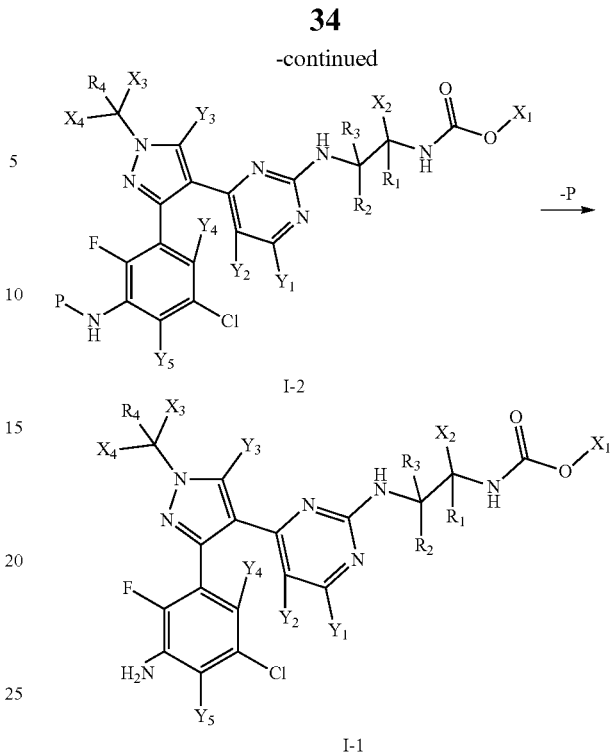

wherein $Y_1$, $Y_2$, $Y_3$, $Y_4$, $Y_5$, $R_1$, $R_2$, $R_3$, $R_4$, $X_1$, $X_2$, $X_3$, $X_4$ and $X_5$ are as defined in the summary of the invention, M is a leaving group (e.g., iodine, bromine, chlorine, trifluoromethanesulfonyloxy, etc.), each Z may be, for example, hydrogen, methyl, etc., or two Z groups may be connected to form a cyclic borate. Both P groups may be hydrogen, or two P groups taken together represent a suitable nitrogen-protecting group (e.g., one P may be hydrogen and the other may be Boc). The compound of formula (I-2) may be prepared by the reaction of the compound of formula (I-4) with the compound of formula (I-3) in the presence of a suitable transition metal catalyst (e.g., Pd(PPh$_3$)$_4$ or PdCl$_2$(dppf)), a suitable solvent (e.g., DME, dioxane, toluene, ethanol, etc.) and a suitable alkali (e.g., anhydrous potassium carbonate or sodium carbonate, etc.). The reaction is carried out at a temperature ranging from about 20° C. to 120° C. and may take about 2 hours to complete. The compound of formula (I) may be synthesized by removing the protective group P from the compound of formula (I-2) (e.g., by treatment with a strong acid such as hydrogen chloride in the presence of DME and dioxane).

The compound of formula (I-4) can be prepared by the following reaction scheme 3:

Reaction scheme 3

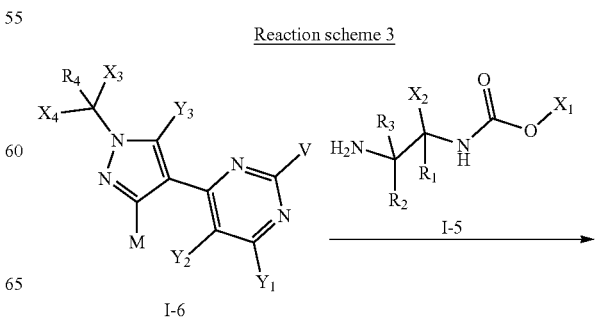

-continued

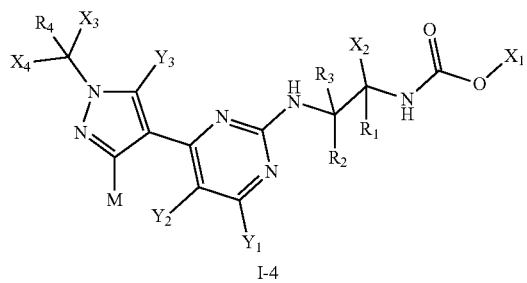

I-4 wherein $Y_1$, $Y_2$, $R_1$, $R_2$, $R_3$, $R_4$, $X_1$, $X_2$, $X_3$ and $X_4$ are as defined in the summary of the invention, M is a leaving group (e.g., iodine, bromine, chlorine, trifluoromethanesulfonyloxy, etc.), and V is a leaving group (e.g., iodine, bromine, chlorine, trifluoromethanesulfonyloxy, etc.). The compound of formula (I-4) may be prepared by the reaction of the amine compound of formula (I-5) with the compound of formula (I-6). The reaction is carried out in the presence of a suitable alkali (e.g., sodium carbonate or potassium carbonate, etc.) in a suitable solvent (e.g., DMSO, NMP, dioxane or isopropanol) at a temperature ranging from about 25° C. to about 120° C.

EXAMPLES

The present disclosure is further illustrated below in conjunction with specific examples. It is to be understood that the examples are used to illustrate the present disclosure, and not intended to limit the scope of present disclosure. In the following examples, the experimental methods wherein the particular conditions are not specified are usually in accordance with conventional conditions or according to the conditions recommended by the manufacturer. Parts and percentages are parts by weight and percentage by weight unless otherwise stated.

| | |
|---|---|
| APCI | Atmospheric pressure chemical ionization |
| HPLC | High performance liquid chromatography |
| TLC | Thin layer chromatography |
| h | Hour |
| DMF | N,N-dimethylformamide |
| $K_2CO_3$ | Potassium carbonate |
| DCM | Dichloromethane |
| THF | Tetrahydrofuran |
| $CH_3MgBr$ | Methylmagnesium bromide |
| PTSA | p-Toluenesulfonic acid |
| TFA | Trifluoroacetic acid |
| NMP | N-Methyl-2-pyrrolidone |
| Diguanidinium carbonate | Guanidinium carbonate |
| MTBE | Methyl tert-butyl ether |
| $POCl_3$ | Phosphoryl chloride |
| DMSO | Dimethyl sulfoxide |
| $Pd(dppf)Cl_2$ | [1,1'-Bis(diphenylphosphino)ferrocene]palladium(II) dichloride |
| Dioxane | 1,4-Dioxane |
| TsCl | 4-Toluenesulfonyl chloride |
| Boc | Tert-butoxycarbonyl |
| DIPEA | N,N-Diisopropylethylamine |
| $CDCl_3$ | Deuterated chloroform |
| TEA | Triethylamine |
| DMAP | 4-Dimethylaminopyridine |
| $Na_2CO_3$ | Sodium carbonate |
| HCl | Hydrochloric acid |
| MsCl | Methanesulfonyl chloride |
| Tol | Toluene |

Intermediate A: Preparation of 2-chloro-4-(3-iodo-1-(propan-2-yl-$d_7$-1H-pyrazol-4-yl)pyrimidine

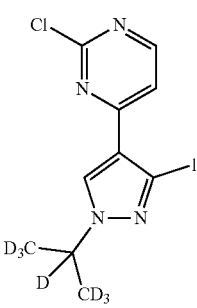

A

The following route was used for the synthesis:

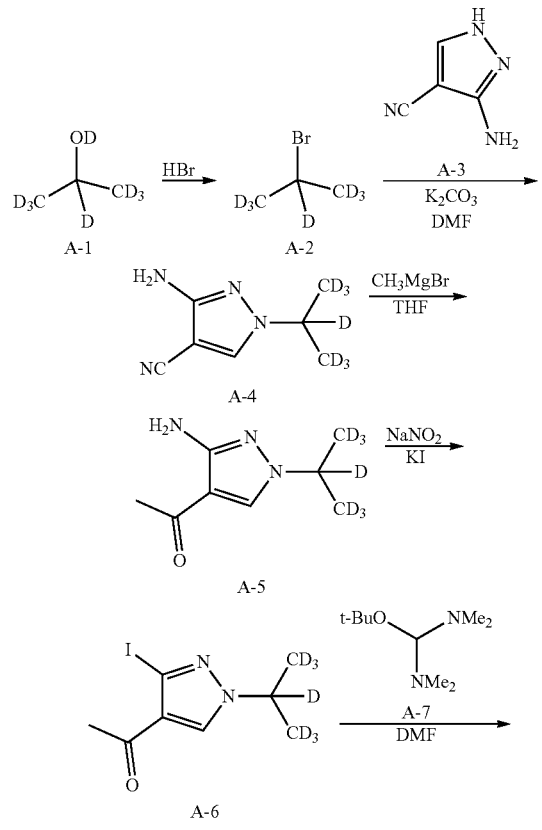

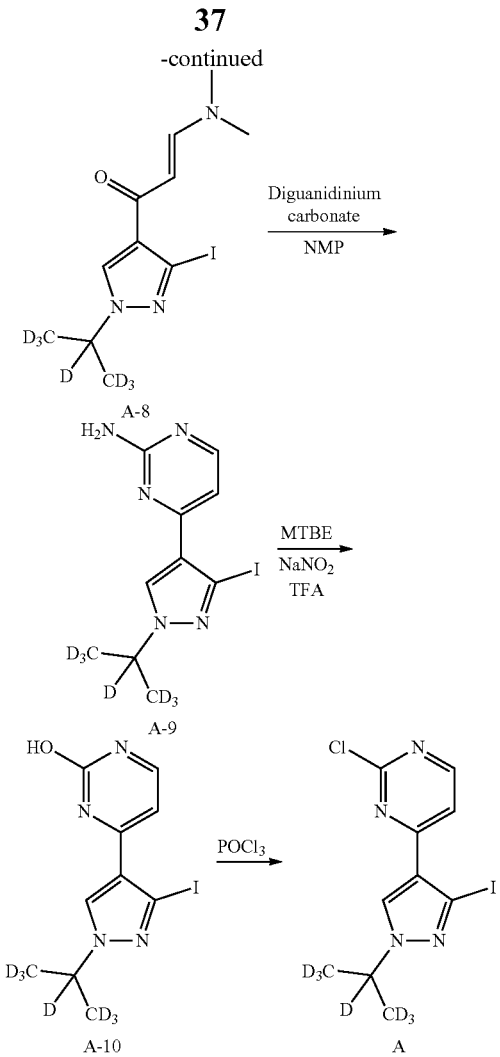

A-8
A-9
A-10
A

Step 1 Synthesis of Compound A-2

Compound 1 (5.0 g, 73.4 mmol) was added to a 47% solution of hydrobromic acid (20 ml), and the reaction solution was reacted at 80° C. for 3 h. Then the reaction solution was distilled under atmospheric pressure, and the fractions between 60° C. and 70° C. were collected to give 6.2 g of colorless liquid, with a yield of 65%.

Step 2 Synthesis of Compound A-4

Compound A-3 (3.0 g, 27.8 mmol) was added to DMF (20 ml), and the resulting solution was cooled to 0° C. Then $K_2CO_3$ (4.6 g, 33.3 mmol, 10 ml) was added, and the resulting solution was stirred at a low temperature for 0.5 h. Compound A-2 (4.3 g, 33.3 mmol) was then slowly added dropwise. After the addition was completed, the resulting solution was heated to 90° C. and reacted for 10 h. The reaction solution was extracted with DCM (50 ml×3). The organic phases were combined, and dried over anhydrous sodium sulfate. The concentrate was separated by column chromatography (eluent: petroleum ether/ethyl acetate (v/v)=1:1) to give 3.1 g of a white solid, with a yield of 72%. LC-MS(APCI):m/z=158.21-96 (M+1)$^+$.

Step 3 Synthesis of Compound A-5

Under nitrogen protection, compound A-4 (3.0 g, 19.1 mmol) was added to anhydrous THF (40 ml), and the resulting solution was cooled to −5° C. Then, a solution of $CH_3MgBr$ in anhydrous THF (19.1 ml, 57.3 mmol, 3 ml/L) was added dropwise. After the addition was completed, the resulting solution was slowly heated to reflux, and reacted for 4 h. The reaction was quenched with saturated ammonium chloride, and the pH was adjusted to neutral with dilute hydrochloric acid. The reaction solution was extracted with ethyl acetate (50 ml×3). The organic phases were combined, and dried over anhydrous sodium sulfate. The concentrate was separated by column chromatography (eluent: petroleum ether/ethyl acetate (v/v)=2:3) to give 2.0 g of a yellow solid, with a yield of 61%. LC-MS(APCI):m/z=175.21(M+1)$^+$.

Step 4 Synthesis of Compound A-6

Compound A-5 (2.0 g, 11.5 mmol) and PTSA (4.2 g, 23.0 mmol) were sequentially added to acetonitrile (15 ml), and the resulting solution was cooled to 0° C. Then a solution of sodium nitrite (1.43 g, 20.7 mmol) and potassium iodide (3.82 g, 23.0 mmol) in water (5 ml) was added dropwise. The reaction solution was reacted at room temperature for 3 h, and extracted with ethyl acetate (30 ml×3). The organic phases were combined, dried over anhydrous sodium sulfate, and rotary evaporated to dryness to give 2.5 g of an orange solid, with a yield of 75%.

Step 5 Synthesis of Compound A-8

Under nitrogen protection, compound A-6 (2.0 g, 7.01 mmol) was added to DMF (15 ml), and the resulting solution was heated to 120° C. Then compound A-7 (1.9 g, 10.5 mmol, 10 ml) was added, and the resulting solution was reacted with stirring at 120° C. for 0.5 h. The reaction solution was extracted with dichloromethane (30 ml×3). The organic phases were combined, and dried over anhydrous sodium sulfate. The concentrate was separated by column chromatography (eluent: petroleum ether/ethyl acetate (v/v) 1:3) to give 1.9 g of product, with a yield of 80%. LC-MS(APCI):m/z=341.06(M+1)$^+$.

Step 6 Synthesis of Compound A-9

Under nitrogen protection, compound A-8 (1.9 g, 5.6 mmol) and diguanidinium carbonate (1.6 g, 12.8 mmol) were sequentially added to NMP (20 ml), and a water separation device was set up at the same time. The resulting solution was heated to 130° C., at which the solution was reacted with stirring for 10 h. After the reaction was completed, the reaction solution was extracted with dichloromethane (30 ml×3). The organic phases were combined, and dried over anhydrous sodium sulfate. The concentrate was separated by column chromatography (eluent: petroleum ether/ethyl acetate (v/v)=2:3) to give 1.5 g of product, with a yield of 81%. LC-MS(APCI):m/z=336.86(M+1)$^+$.

Step 7 Synthesis of Compound A-10

Compound A-9 (1.5 g, 4.5 mmol) was added to TFA (15 ml), and the resulting solution was cooled to 0° C. Then sodium nitrite (0.93 g, 13.4 mmol) was added as a solid, and the reaction solution was reacted at room temperature for 1 h. The reaction solution was extracted with ethyl acetate (30 ml×3). The organic phases were combined, and dried over anhydrous sodium sulfate. The mixture was rotary evaporated to dryness, and the resulting oil was slurried with MTBE (10 ml). The slurry was filtered to give 1.3 g of a white solid, with a yield of 87%. LC-MS(APCI):m/z=338.15(M+1)⁺.

Step 8 Synthesis of Intermediate Compound a

Compound A-10 (1.3 g, 3.86 mmol) was added to POCl₃ (15 ml), and the resulting solution was heated to 110° C., and the resulting solution was reacted under reflux at this temperature for 10 h. After the reaction was completed, the reaction solution was rotary evaporated to dryness. The reaction solution was extracted with dichloromethane (30 ml×2). The organic phases were combined, and dried over anhydrous sodium sulfate. The concentrate was separated by column chromatography (eluent: petroleum ether/ethyl acetate (v/v)=4:1) to give 1.0 g of product, with a yield of 73%. LC-MS(APCI):m/z=356.32(M+1)⁺.

Intermediate B: Preparation of (S)-(methyl-d₃)(1-aminopropan-2-yl)carbamate

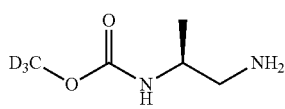

The following route was used for the synthesis:

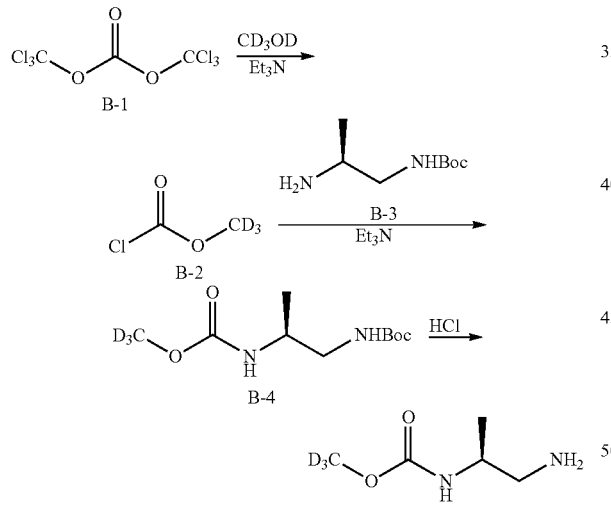

Step 1 Synthesis of Compound B-2

Compound B-1 (1.3 g, 4.5 mmol) was dissolved in toluene (15 ml) and the resulting solution was cooled to 0° C. Then a solution of CD₃OD (0.5 g, 15 mmol) and triethylamine (1.7 g, 17 mmol) in toluene (10 ml) was added dropwise. After the addition was completed, the resulting solution was reacted at room temperature for 2 h. The resulting mixture was washed three times with ice-water, dried over anhydrous sodium sulfate, and filtered to give a solution of compound B-2 in toluene, which was directly used in the next step.

Step 2 Synthesis of Compound B-4

Compound B-3 hydrochloride (0.5 g, 2.4 mmol) and triethylamine (0.73 g, 7.2 mmol) were sequentially added to dichloromethane (10 ml) at 0° C. Then the solution of compound B-2 in toluene from the previous step was added dropwise. After the addition was completed, the resulting solution was reacted at room temperature for 5 h. The reaction solution was quenched with water (10 ml), and extracted with dichloromethane (20 ml×3). The organic phases were combined, and dried over anhydrous sodium sulfate. The concentrate was separated by column chromatography (eluent: petroleum ether/ethyl acetate (v/v)=4:1) to give 0.45 g of a white solid product, with a yield of 80%.

Step 3 Synthesis of Intermediate Compound B

A 4 M solution of hydrochloric acid in dioxane (4 ml) was slowly added to a solution of compound B-4 (0.45 g, 1.9 mmol) in dichloromethane (10 ml) at 0° C. The resulting solution was warmed to room temperature, and further reacted for 6 h. After the reaction was completed, the solution was rotary evaporated to dryness. The residue was slurried with petroleum ether (10 ml), and filtered with suction to give 0.2 g of product, with a yield of 77%.

Intermediate C: Preparation of methyl (1-aminopropan-2-yl-1,1,3,3,3-d₅)carbamate

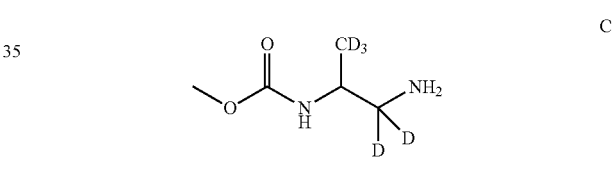

The following route was used for the synthesis:

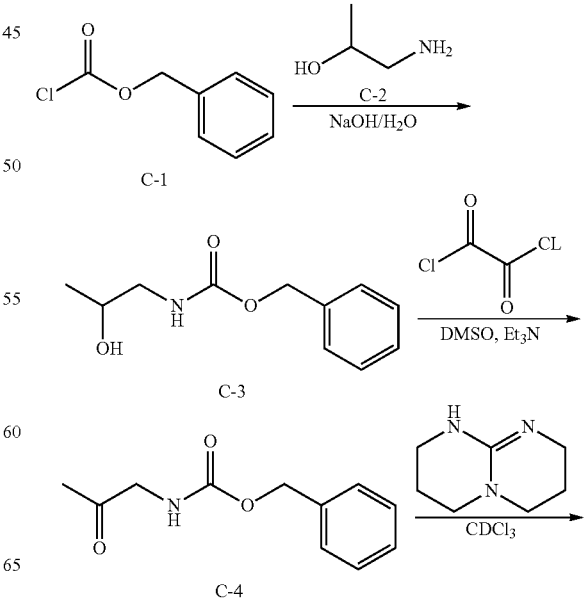

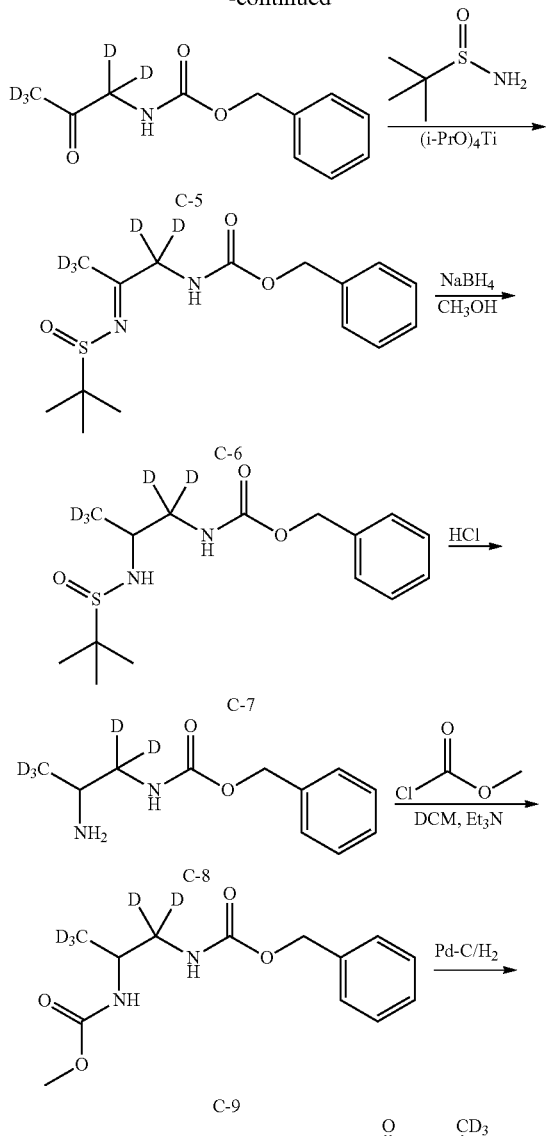

Step 1 Synthesis of Compound C-3

A mixture of compound C-2 (4.6 g, 61.8 mmol) compound C-1 (11.5 g, 67.6 mmol) and sodium hydroxide (7.16 g, 67.7 mmol) in water (60 ml) was reacted with stirring at 0° C. for 3 h. After the reaction was completed, water (60 ml) was added, and the resulting solution was extracted with ethyl acetate (60 ml×3). The organic phases were combined, and dried over anhydrous sodium sulfate. The concentrate was separated by column chromatography (eluent: petroleum ether/ethyl acetate (v/v)=10:1) to give 11.2 g of oily product, with a yield of 88%.

Step 2 Synthesis of Compound C-4

Under nitrogen atmosphere, DMSO (4.8 g, 61.5 mmol) was slowly added to a solution of oxalyl chloride (6.0 g, 47.2 mmol) in DCM (60 ml) at −78° C., and the resulting mixture was stirred at −78° C. for half an hour. A solution of compound C-3 (8.0 g, 38.2 mmol) in DCM (20 ml) was added to the mixture, and the resulting mixture was further stirred at −78° C. for 1 h. Then triethylamine (16 ml) was added to the mixture. The resulting mixture was warmed to room temperature, and washed sequentially with IN hydrochloric acid (50 ml) and aqueous sodium bicarbonate solution (50 ml). The organic phase was dried over anhydrous sodium sulfate, concentrated by heating, and slurried with a mixture of PE and EA with a volume ratio of 8:1 (PE:EA) to give 5.3 g of a white solid product, with a yield of 87%.

Step 3 Synthesis of Compound C-5

1,5,7-Triazabicyclo[4.4.0]dec-5-ene (0.27 g, 1.9 mmol) was added to a solution of compound C-4 (4.0 g, 19.3 mmol) in deuterated chloroform (30 ml), and the reaction solution was stirred at room temperature for 30 h. The reaction solution was then quenched with water (10 ml). The organic phase was separated and washed with saturated sodium chloride solution. The organic phase was dried, and then rotary evaporated to dryness to give 3.9 g of oily product, with a yield of 98%.

Step 4 Synthesis of Compound C-6

Under nitrogen atmosphere, compound C-5 (4.0 g, 18.9 mmol) and tert-butanesulfinamide (2.7 g, 22.6 mmol) were sequentially added to THE (60 ml), and then tetraisopropyl titanate (11.8 g, 41.5 mmol) was added at room temperature. The resulting solution was heated to 60° C. and reacted for 3 h. The reaction solution was cooled to room temperature, quenched with water, and extracted with ethyl acetate (60 ml×3). The organic phases were combined, and dried over anhydrous sodium sulfate. The concentrate was separated by column chromatography (eluent: petroleum ether/ethyl acetate (v/v)=4:1) to give 3.5 g of product, with a yield of 58%. LC-MS(APCI): m/z=315.80(M+1)$^+$.

Step 5 Synthesis of Compound C-7

NaBH$_4$ (0.73 g, 19.1 mmol) was added to a solution of compound C-6 (2.0 g, 6.3 mmol) in methanol (20 ml) at −50° C. and the resulting solution was further reacted at the low temperature for 1 h. The reaction solution was quenched with 1 M hydrochloric acid, and extracted with dichloromethane (30 ml×2). The organic phases were combined, dried over anhydrous sodium sulfate, and filtered. The filtrate was rotary evaporated to dryness to give 2.1 g of oily product, which was directly used in the next step.

Step 6 Synthesis of Compound C-8

A 4 M solution of hydrochloric acid in dioxane (10 ml) was slowly added to a solution of compound C-7 (2.0 g, 6.3 mmol) in dichloromethane (20 ml) at 0° C. The resulting solution was reacted at 0° C. for 6 h. After the reaction was completed, the solution was rotary evaporated to dryness, and the resulting product was directly used in the next step without further treatment.

Step 7 Synthesis of Compound C-9

Triethylamine (1.43 g, 14.1 mmol) was added to a solution of compound C-8 (1.5 g, 7.0 mmol) in dichloromethane (20 ml) at 0° C., and methyl chloroformate (0.8 g, 8.5 mmol)

was added dropwise to the mixture. After the addition was completed, the resulting mixture was reacted at room temperature for 5 hours. After the reaction was completed, the reaction solution was quenched with water (10 ml), and extracted with dichloromethane (20 ml×2). The organic phases were combined, and dried over anhydrous sodium sulfate. The concentrate was separated by column chromatography (eluent: petroleum ether/ethyl acetate (v/v)=4:1) to give 1.1 g of a white solid product, with a yield of 58%.

Step 8 Synthesis of Intermediate Compound C

Under the hydrogen atmosphere, Pd-C (0.2 g, 10%) was added to a solution of compound C-9 (1.0 g, 3.7 mmol) in ethanol (5 ml) and 1 N hydrochloric acid (5 ml), and the resulting solution was reacted with stirring for 5 h. After the reaction was completed, the resulting mixture was filtered, and the filtrate was directly concentrated to give 0.4 g of product.

Example 1 Preparation of (S)-methyl (1((4-(3-(5-chloro-2-fluoro-3-(methylsulfonamido)phenyl)-1-(propan-2-yl-d₇)-1H-pyraz ol-4-yl)pyrimidin-2-yl)amino)propan-2-yl)carbamate (compound L-1)

The following route was used for the synthesis:

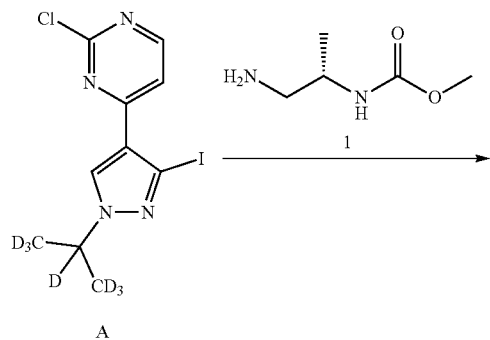

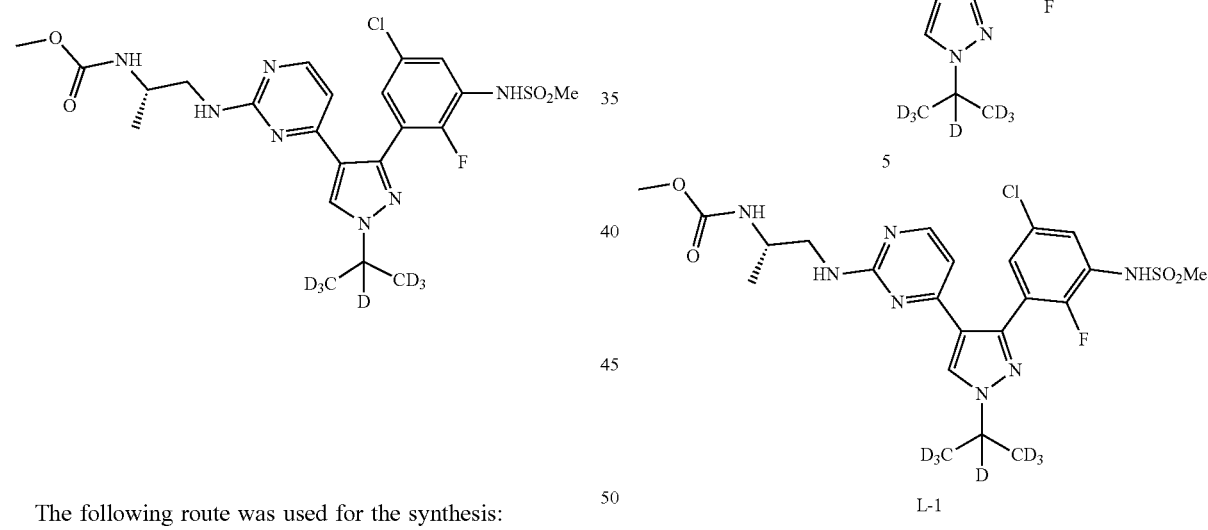

Step 1 Synthesis of Compound 2

Under nitrogen protection, intermediate compound A (1.0 g, 2.8 mmol), compound 1 (0.52 g, 3.1 mmol), and sodium carbonate (1.2 g, 11.2 mmol) were sequentially added to DMSO (20 ml). The resulting solution was heated to 90° C., and reacted at this temperature with stirring for 16 h. After the reaction was completed, the reaction solution was extracted with DCM (30 ml×3). The organic phases were combined, and dried over anhydrous sodium sulfate. The concentrate was separated by column chromatography (eluent: petroleum ether/ethyl acetate (v/v) 1:2) to give 0.8 g of product, with a yield of 63%. LC-MS(APCI):m/z=452.33 (M+1)⁺.

Step 2 Synthesis of Compound 4

Under nitrogen protection, compound 2 (0.5 g, 1.11 mmol), compound 3 (0.5 g, 1.33 mmol), sodium carbonate (0.47 g, 4.43 mmol), and Pd(dppf)Cl$_2$ (0.09 g, 0.11 mmol) were sequentially added to a mixed solution of toluene (20 ml) and water (4 ml). The resulting solution was heated to 80° C. and reacted for 2 h. The reaction solution was cooled to room temperature, and extracted with ethyl acetate (30 ml×3). The organic phases were combined, and dried over anhydrous sodium sulfate. The concentrate was separated by column chromatography (eluent: petroleum ether/ethyl acetate (v/V)=1:1) to give 0.2 g of product, with a yield of 31%. LC-MS(APCI):m/z=569.09(M+1)$^+$.

Step 3 Synthesis of Compound 5

A 4 M solution of hydrochloric acid in dioxane (4 ml) was slowly added to a solution of compound 4 (0.2 g, 0.35 mmol) in DCM (10 ml) at 0° C. The resulting solution was warmed to room temperature and further reacted for 6 h. After the reaction was completed, the solution was rotary evaporated to dryness, and the resulting product was directly used in the next step without further treatment. LC-MS(APCI):m/z=469.27(M+1)$^+$.

Step 4 Synthesis of Compound L-1

Compound 5 (0.15 g, 0.32 mmol) and triethylamine (0.16 g, 1.6 mmol) were sequentially added to DCM (10 ml). The resulting solution was cooled to 0° C., and MsCl (0.11 g, 1.0 mmol) was slowly added dropwise. After the addition was completed, the resulting solution was warmed to room temperature and reacted for 5 h. After the reaction was completed, the reaction solution was directly rotary evaporated to dryness to give a residue. Then toluene (9 ml), methanol (1 ml), water (10 ml), and sodium carbonate (2 g) were sequentially added to the residue. The resulting solution was heated to 85° C., and reacted for 10 hours. The resulting solution was cooled to room temperature, and extracted with ethyl acetate (20 ml×3). The organic phases were combined, and dried over anhydrous sodium sulfate. The concentrate was separated by column chromatography (eluent: dichloromethane/methanol (v/v)=20:1) to give 50 mg of product, with a yield of 35%. LC-MS(APCI):m/z=547.31(M+1)$^+$. $^1$H NMR (400 MHz, CDCl$_3$) δ 8.08 (d, J=11.4 Hz, 2H), 7.61 (d, J=6.3 Hz, 1H), 7.42 (d, J=5.6 Hz, 1H), 6.48 (d, J=5.1 Hz, 1H), 532 (d, J=18.8 Hz, 1H), 5.17 (s, 1H), 4.59 (d, J=13.2 Hz, 1H), 3.79 (s, 1H), 3.61 (s, 3H), 3.24 (s, 1H), 2.98 (d, J=16.6 Hz, 3H), 2.01 (s, 1H), 1.31 (s, 3H).

Example 2 Preparation of (S)-(methyl-d$_3$) (1-((4-(3-(5-chloro-2-fluoro-3-(methylsulfonamido)phenyl)-1-isopropyl-1H-pyrazol-4-yl) pyrimidin-2-yl)amino)propan-2-yl)carbamate (compound L-2)

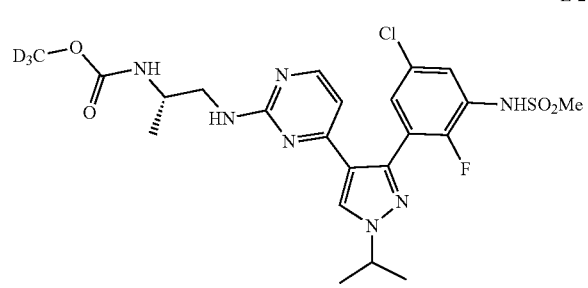

L-2

The following route was used for the synthesis:

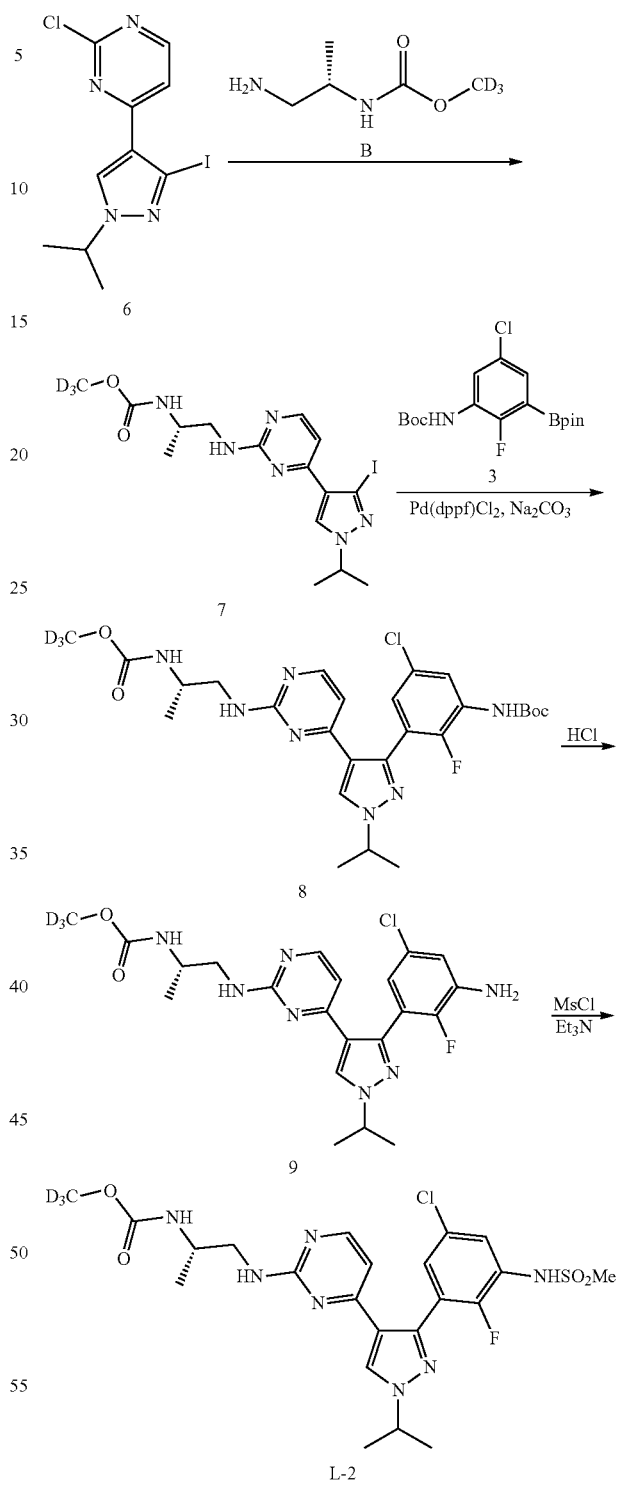

Step 1 Synthesis of Compound 7

Under nitrogen protection, compound 6 (0.5 g, 1.5 mmol), intermediate compound B (0.2 g, 1.5 mmol) and sodium carbonate (0.63 g, 6.0 mmol) were sequentially added to DMSO (20 ml). The resulting solution was heated to 90° C., and the resulting solution was reacted at this temperature with stirring for 16 h. After the reaction was completed, the reaction solution was extracted with DCM (30 ml×3). The organic phases were combined, and dried over anhydrous sodium sulfate. The concentrate was separated by column chromatography (eluent: petroleum ether/ethyl acetate (v/v)=1:2) to give 0.42 g of product, with a yield of 65%, LC-MS(APCI): m/z=447.80(M+1)+.

Step 2 Synthesis of Compound 8

Under nitrogen protection, compound 7 (0.4 g, 0.90 mmol), compound 3 (0.4 g, 1.07 mmol), sodium carbonate (0.38 g, 3.6 mmol), and Pd(dppf)Cl$_2$ (0.07 g, 0.09 mmol) were sequentially added to a mixed solution of toluene (20 ml) and water (4 ml). The resulting solution was heated to 80° C. and reacted for 2 h. The reaction solution was cooled to room temperature, and extracted with ethyl acetate (30 ml×3). The organic phases were combined, and dried over anhydrous sodium sulfate. The concentrate was separated by column chromatography (eluent: petroleum ether/ethyl acetate (v/v)=1:1) to give 0.2 g of product, with a yield of 40%. LC-MS(APCI): m/z=565.03(M+1)+.

Step 3 Synthesis of Compound 9

A 4 M solution of hydrochloric acid in dioxane (4 ml) was slowly added to a solution of compound 8 (0.2 g, 0.35 mmol) in DCM (10 ml) at 0° C. The resulting solution was warmed to room temperature and further reacted for 6 h. After the reaction was completed, the solution was rotary evaporated to dryness, and the resulting product was directly used in the next step without further treatment. LC-MS(APCI):m/z=465.27 (M+1)+.

Step 4 Synthesis of Compound L-2

Compound 9 (0.2 g, 0.43 mmol) and triethylamine (0.22 g, 2.1 mmol) were sequentially added to DCM (10). The resulting solution was cooled to 0° C., and MsCl (0.15 g, 1.3 mmol) was slowly added dropwise. After the addition was completed, the resulting solution was warmed to room temperature and reacted for 5 h. After the reaction was completed, the reaction solution was directly rotary evaporated to dryness to give a residue. Then toluene (9 ml), methanol (1 ml), water (10 m), and sodium carbonate (2 g) were sequentially added to the residue. The resulting solution was heated to 85° C., and reacted for 10 hours. The resulting solution was cooled to room temperature, and extracted with ethyl acetate (20 ml×3). The organic phases were combined, and dried over anhydrous sodium sulfate. The concentrate was separated by column chromatography (eluent: dichloromethane/methanol (v/v)=20:1) to give 70 mg of product, with a yield of 30%. LC-MS(APCI): m/z=543.21(M+1)+. $^1$H NMR (400 MHz, CDCl$_3$) δ 8.01 (d, J=11.4 Hz, 2H), 7.63 (d, J=6.3 Hz, 1H), 7.40 (d, J=5.8 Hz, 1H), δ 58 (d, J=6.1 Hz, 1H), 5.47 (d, J=18.8 Hz, 1H), 5.17 (s, 1H), 4.59 (d, J=: 12.2, Hz, 1H), 3.80 (s, 1H), 3.61 (s, 1H) 3.24 (s, 1H), 3.10 (d, J=16.6 Hz, 3H), 2.21 (s, 1H), 1.35 (s, 3H), 1.27 (d, 6H).

Example 3 Preparation of (S)-(methyl-d$_3$) 1-((4-(3-(5-chloro-2-fluoro-3-methylsulfonamido)phenyl)-1-(propan-2-yl-d$_7$)-1H-pyraz ol-4-yl)pyrimidin-2-yl)amino)propan-2-yl)carbamate (compound L-3)

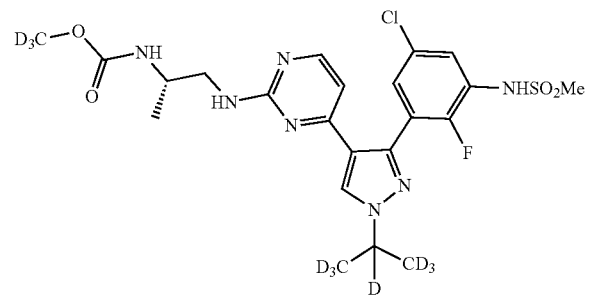

The following route was used for the synthesis:

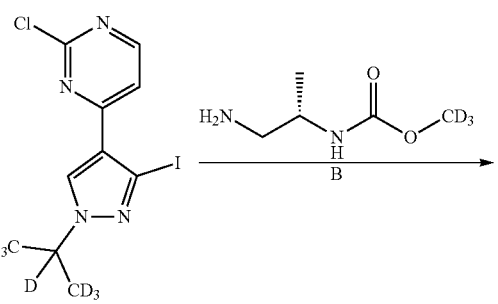

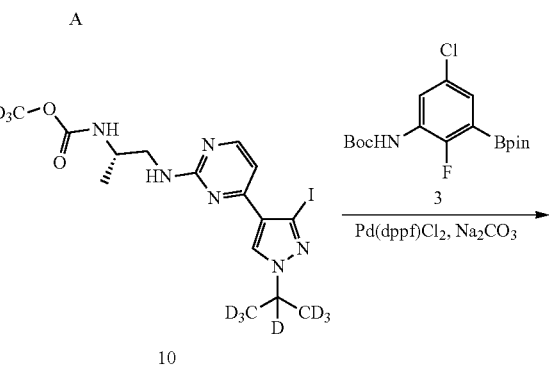

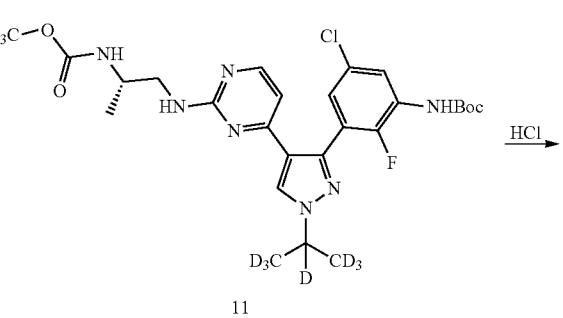

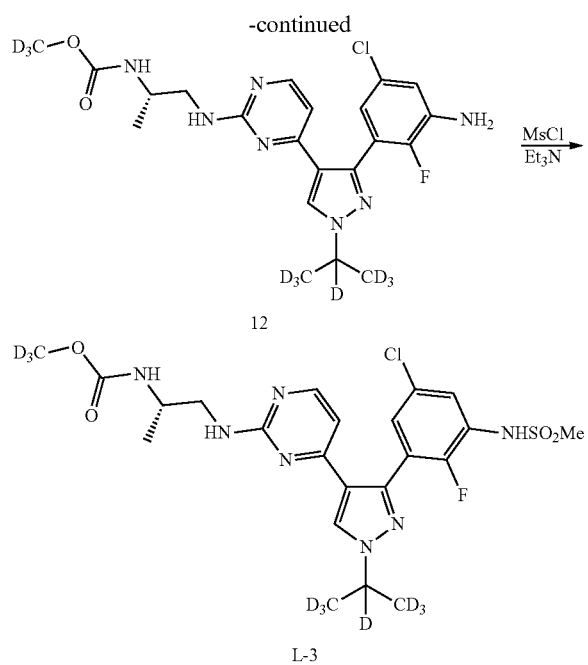

Step 4 Synthesis of Compound L-3

Compound 12 (0.25 g, 0.53 mmol) and triethylamine (0.27 g, 2.6 mmol) were sequentially added to DCM (10 ml). The resulting solution was cooled to 0° C., and MsCl (0.18 g, 1.6 mmol) was slowly added dropwise, After the addition was completed, the resulting solution was warmed to room temperature and reacted for 5 h. After the reaction was completed, the reaction solution was directly rotary evaporated to dryness to give a residue. Then toluene (9 ml), methanol (1 ml), water (10 ml), and sodium carbonate (2 g) were sequentially added to the residue. The resulting solution was heated to 85° C., and reacted for 10 hours. The resulting solution was cooled to room temperature, and extracted with ethyl acetate (20 ml×3). The organic phases were combined, and dried over anhydrous sodium sulfate. The concentrate was separated by column chromatography (eluent: dichloromethane/methanol (v/v)=20:1) to give 75 mg of product, with a yield of 26%. LC-MS(APCI): m/z=550.29(M+1)$^+$. $^1$H NMR (400 MHz, CDCl$_3$) δ 8.13 (d, J=11.4 Hz, 2H), 7.63 (d, J=6.3 Hz, 1H) 7.40 (d, J=5.8 Hz, 1H), 6.65 (d, J=6.1 Hz, 1H), 5.47 (d, J=18.8 Hz, 1H), 5.17 (s, 1H), 4.63 (d, J=12.2, Hz, 1H), 3.70 (s, 1H), 3.54 (s, 1H), 3.16 (d, J=16.6 Hz, 3H), 2.11 (s, 1H), 1.38 (s, 3H).

Step 1 Synthesis of Compound 10

Under nitrogen protection, intermediate compound A (0.6 g, 1.7 mmol), intermediate compound B (0.23 g, 1.7 mmol), and sodium carbonate (0.71 g, 6.8 mmol) were sequentially added to DMSO (20 ml). The resulting solution was heated to 90° C. and the resulting solution was reacted at this temperature with stirring for 16 h, After the reaction was completed, the reaction solution was extracted with DCM (30 ml×3). The organic phases were combined, and dried over anhydrous sodium sulfate. The concentrate was separated by column chromatography (eluent: petroleum ether-ethyl acetate (v/v) 1:2) to give 0.65 g of product, with a yield of 84%. LC-MS(APCI): m/z=454.92(M+1)$^+$.

Step 2 Synthesis of Compound 11

Under nitrogen protection, compound 10 (0.6 g, 1.3 mmol), compound 3 (0.59 g, 1.6 mmol), sodium carbonate (0.56 g, 5.3 mmol), and Pd(dppf)Cl$_2$ (0.10 g, 0.13 mmol) were sequentially added to a mixed solution of toluene (20 ml) and water (4 ml). The resulting solution was heated to 80° C. and reacted for 2 h. The reaction solution was cooled to room temperature, and extracted with ethyl acetate (30 ml×3). The organic phases were combined, and dried over anhydrous sodium sulfate. The concentrate was separated by column chromatography (eluent: petroleum ether/ethyl acetate (v/v)=1:1) to give 0.32 g of product, with a yield of 43%. LC-MS(APCI): m/z=572.10(M+1)$^+$.

Step 3 Synthesis of Compound 12

A 4 M solution of hydrochloric acid in dioxane (4 ml) was slowly added to a solution of compound 11 (0.3 g, 0.52 mmol) in DCM (10 ml) at 0° C. The resulting solution was warmed to room temperature and further reacted for 6 h. After the reaction was completed, the solution was rotary evaporated to dryness, and the resulting product was directly used in the next step without further treatment, LC-MS (APCI):m/z=472.09(M+1)$^+$.

Example 4 Preparation of methyl (1-((4-(3-(5-chloro-2-fluoro-3-(methylsulfonamido)phenyl)-1-(propan-2-yl)-1H-pyrazol-4-yl)pyrimidin-2-yl)amino)propan-2-yl-1,1,3,3,3-d$_5$)carbamate (compound L-4, (S)-methyl (1-((4-(3-(5-chloro-2-fluoro-3-(methylsulfonamido)phenyl)-1-(propan-2-yl)-1H-pyrazol-4-yl)pyrimidin-2-yl)amino)propan-2-yl-1,1,3,3,3-d$_5$)carbamate (compound L-4-S), and (R)-methyl (1-((4-(3-(5-chloro-2-fluoro-3-(methylsulfonamido)phenyl)-1-(propan-2-yl)-1H-pyrazol-4-yl)pyrimidin-2-yl)amino)propan-2-yl-1,1,3,3,3-d$_5$) carbamate (compound L-4-R)

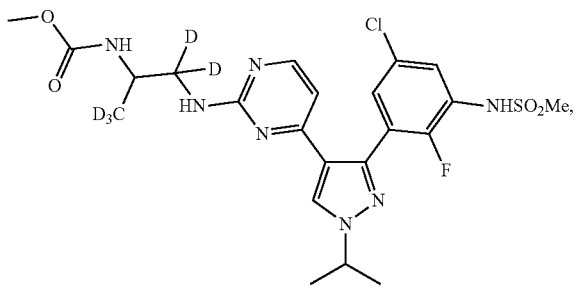

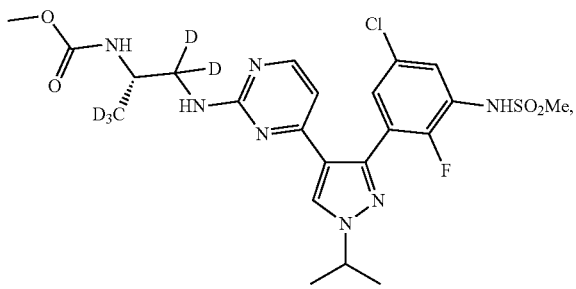

L-4-R

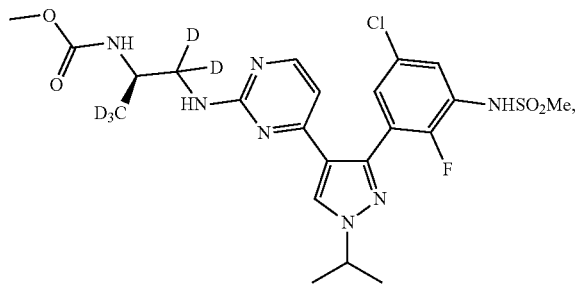

The following route was used for the synthesis:

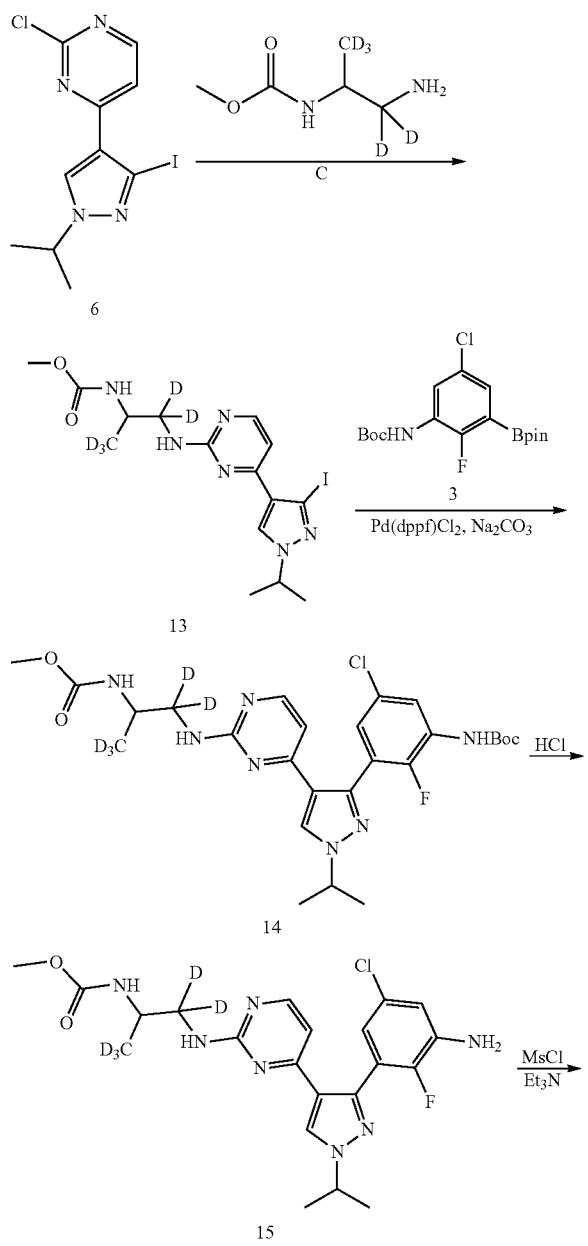

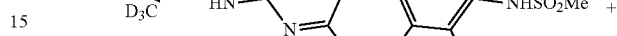

L-4

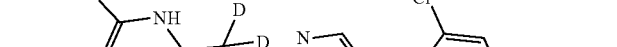

L-4-S

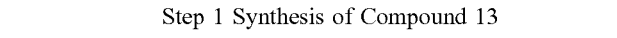

L-4-R

Step 1 Synthesis of Compound 13

Under nitrogen protection, compound 6 (0.4 g, 1.1 mmol), intermediate compound C (0.16 g, 1.1 mmol), and sodium carbonate (0.50 g, 4.6 mmol) were sequentially added to DMSO (15 ml). The resulting solution was heated to 90° C., and the resulting solution was reacted at this temperature with stirring for 16 h. After the reaction was completed, the reaction solution was extracted with dichloromethane (30 ml 3). The organic phases were combined, and dried over anhydrous sodium sulfate. The concentrate was separated by column chromatography (eluent: petroleum ether/ethyl acetate (v/v)=1:2) to give 0.40 g of product, with a yield of 75%. LC-MS(APCI): m/z=44953(M+1)$^+$.

Step 2 Synthesis of Compound 14

Under nitrogen atmosphere, compound 13 (0.4 g, 0.9 mmol), compound 3 (0.5 g, 1.4 mmol), sodium carbonate (0.40 g, 3.56 mmol), and Pd(dppf)Cl$_2$ (0.08 g, 0.1 mmol) were sequentially added to a mixed solution of toluene (20 ml) and water (4 ml). The resulting solution was heated to 80° C. and reacted for 2 h. The reaction solution was cooled to room temperature, and extracted with ethyl acetate (30 ml×3). The organic phases were combined, and dried over anhydrous sodium sulfate. The concentrate was separated by column chromatography (eluent: petroleum ether/ethyl acetate (v/v)=1:1) to give 0.28 g of product, with a yield of 55%, LC-MS(APCI): m/z=567.12(M+1)$^+$.

Step 3 Synthesis of Compound 15

A 4 M solution of hydrochloric acid in dioxane (2 ml) was slowly added to a solution of compound 14 (0.28 g, 0.50 mmol) in dichloromethane (10 ml) at 0° C. The resulting solution was warmed to room temperature and further reacted for 6 h. After the reaction was completed, the solution was directly rotary evaporated to dryness, and the resulting product was directly used in the next step without further treatment. LC-MS(APCI): m/z=467.29(M+1)$^+$.

Step 4 Synthesis of Compound L-4

Triethylamine (0.13 g, 1.28 mmol) was added to a solution of compound 15 (0.2 g, 0.43 mmol) in dichloromethane (10 ml). The resulting solution was cooled to 0° C., and then methanesulfonyl chloride (0.15 g, 1.3 mmol) was slowly added dropwise to the solution. The reaction solution was reacted at room temperature for 5 h. After the reaction was completed, the reaction solution was directly rotary evaporated to dryness. Then toluene (9 ml), methanol (1 ml), water (10 ml), and sodium carbonate (2 g) were added to the residue. The resulting solution was reacted at 85° C. for 10 h. The reaction solution was cooled to room temperature, and extracted with ethyl acetate (20 ml×3). The organic phases were combined, and dried over anhydrous sodium sulfate. The concentrate was separated by column chromatography (eluent: dichloromethane/methanol (v/v)=20:1) to give 65 mg of product, with a yield of 27%. LC-MS(APCI): m/z=545.08(M+1)$^+$, $^1$H NMR (400 MHz, CDCl$_3$) δ 8.05 (d, 2H), 7.61 (d, 1H), 7.45 (d, 1H), 6.40 (d, 1H), 5.29 (d, 1H), 5.18 (s, 1H), 4.62 (d, 1H), 3.89 (d, 1H), 3.58 (s, 3H), 3.10 (d, 31H), 2.05 (s, 1H), 1.29 (d, 6H).

Step 5 Synthesis of Compound L-4-S and Compound L-4-R

The racemate compound L-4 was separated using a chiral preparative column to give compound L-4-S and compound L-4-R.

Example 5 Preparation of methyl (1-((4-(3-(5-chloro-2-fluoro-3-(methylsulfonamido)phenyl)-1-(propan-2-yl-d$_7$)-1H-pyrazol-4-yl)pyrimidin-2-yl)amino)propan-2-yl-1,1,3,3,3-d$_5$)carbamate (compound L-5), (S)-methyl (1-((4-(3-(5-chloro-2-fluoro-3-(methylsulfonamido)phenyl)-1-(propan-2-yl-d$_7$)-3-1H-pyrazol-4-yl)pyrimidin-2-yl)amino) propan-2-yl-1,1,3,3,3-d$_5$)carbamate (compound L-5-S), and (R)-methyl (1-((4-(3-(5-chloro-2-fluoro-3-(methylsulfonamido)phenyl)-1-(propan-2-yl-d$_7$)-1H-pyrazol-4-yl)pyrimidin-2-yl)amino)propan-2-yl-1,1,3,3,3-d$_5$)carbamate (compound L-5-R)

L-5

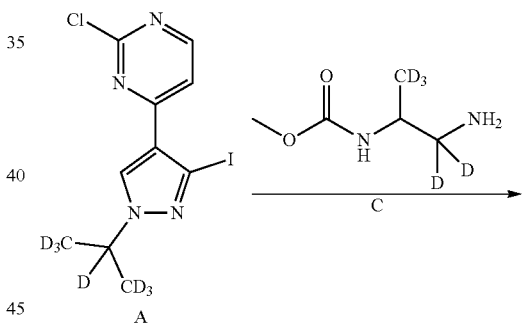

L-5-S

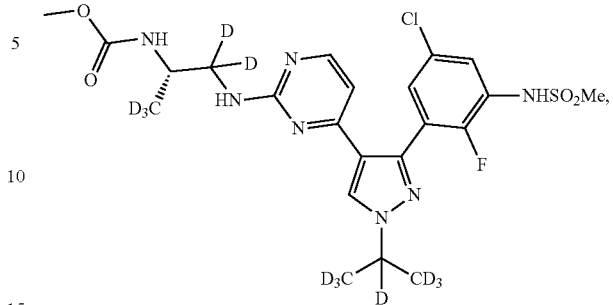

L-5-R

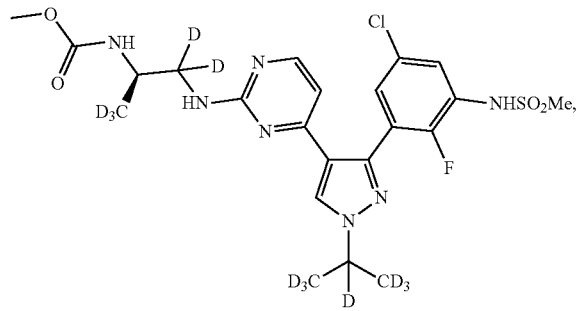

The following route was used for the synthesis:

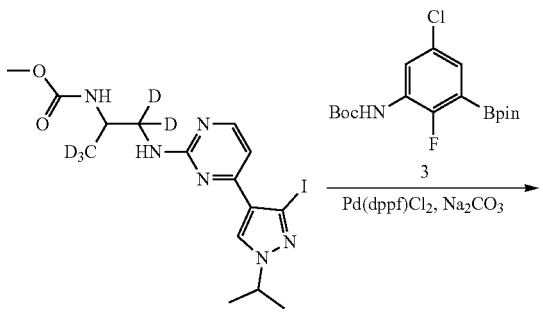

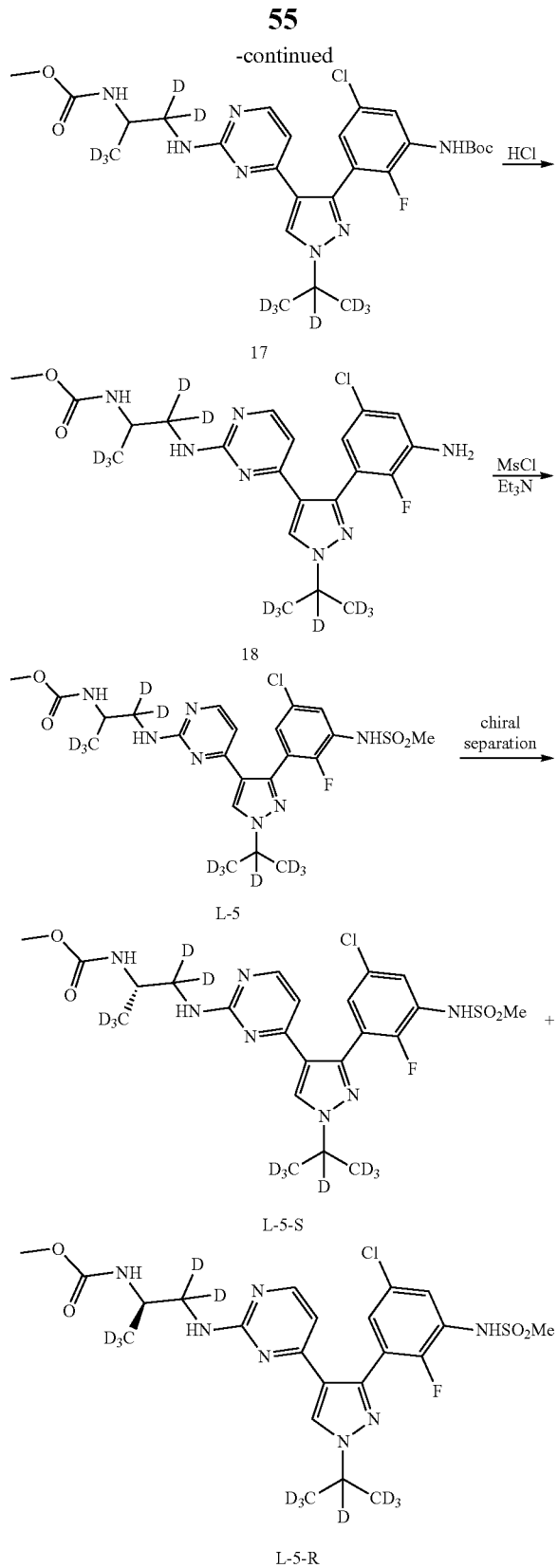

and sodium carbonate (0.63 g, 6.0 mmol) were sequentially added to DMSO (20 ml). The resulting solution was heated to 90° C., and the resulting solution was reacted at this temperature with stirring for 16 h. After the reaction was completed, the reaction solution was extracted with dichloromethane (30 ml×3). The organic phases were combined, and dried over anhydrous sodium sulfate. The concentrate was separated by column chromatography (eluent: petroleum ether/ethyl acetate (v/v)=1:2) to give 0.45 g of product, with a yield of 68%. LC-MS(APCI): m/z=456.68(M+1)$^+$.

Step 2 Synthesis of Compound 17

Under nitrogen atmosphere, compound 16 (0.45 g, 0.98 mmol), compound 3 (0.55 g, 1.54 mmol), sodium carbonate (0.42 g, 3.95 mmol), and Pd(dppf)Cl$_2$ (0.08 g, 0.1 mmol) were sequentially added to a mixed solution of toluene (20 ml) and water (4 ml). The resulting solution was heated to 80° C. and reacted for 2 h. The reaction solution was cooled to room temperature, and extracted with ethyl acetate (30 ml×3). The organic phases were combined, and dried over anhydrous sodium sulfate. The concentrate was separated by column chromatography (eluent: petroleum ether/ethyl acetate (v/v)=1:1) to give 0.40 g of product, with a yield of 70%, LC-MS(APCI): m/z=574.16(M+1)$^+$.

Step 3 Synthesis of Compound 18

A 4 M solution of hydrochloric acid in dioxane (2 ml) was slowly added to a solution of compound 17 (0.40 g, 0.70 mmol) in dichloromethane (10 ml) at 0° C. The resulting solution was warmed to room temperature and further reacted for 6 h. After the reaction was completed, the solution was directly rotary evaporated to dryness, and the resulting product was directly used in the next step without further treatment. LC-MS(APCI): m/z=474.21(M+1)$^+$.

Step 4 Synthesis of Compound L-5

Triethylamine (0.23 g, 2.21 mmol) was added to a solution of compound 18 (0.35 g, 0.74 mmol) in dichloromethane (10 ml). The resulting solution was cooled to 0° C., and methanesulfonyl chloride (0.25 g, 2.2 mmol) was slowly added dropwise to the solution. The reaction solution was reacted at room temperature for 5 h. After the reaction was completed, the reaction solution was directly rotary evaporated to dryness. Then toluene (9 ml), methanol (1 ml), water (10 ml), and sodium carbonate (2 g) were added to the residue. The resulting solution was reacted at 85° C. for 10 h. The reaction solution was cooled to room temperature, and extracted with ethyl acetate (20 ml×3). The organic phases were combined, and dried over anhydrous sodium sulfate. The concentrate was separated by column chromatography (eluent: dichloromethane/methanol (v/v)=20:1) to give 120 mg of product, with a yield of 30%. LC-MS (APCI): m/z=552.33(M+1)$^+$. $^1$H NMR (400 MHz, CDCl$_3$) δ 8.02 (d, 2H), 7.61 (d, 1H), 7.45 (d, 11H), 6.40 (d, 1H), 5.22 (d, 1H), 5.18 (s, 1H), 4.59 (d, 1H), 3.58 (s, 3H), 298 (d, 3H), 2.05 (s, 1H).

Step 5 Synthesis of Compound L-5-S and Compound L-5-R

The racemate compound L-5 was separated using a chiral preparative column to give compound L-5-S and compound L-5-R.

Step 1 Synthesis of Compound 16

Under nitrogen protection, intermediate compound A (0.5 g, 1.5 mmol), intermediate compound C (0.2 g, 1.5 mmol), Biological Activity Assay (1) Kinase Activity Assay Inhibitory activities of test compounds against BRAF (Invitrogen, PV3848), cRAF (BPS Bioscience, 40008) and BRAF (V600E) (Invitrogen, 40533) were determined using ADP-GloTM Kinase Assay kit (Promega, V9102).

The compounds were 3-fold serially diluted with DMSO (MP, 196055), respectively, each with 10 concentrations. 100 ml of compound diluents and 2.5 μL of BRAF or cRAF or BRAF (V600E) were added to each well of a 384-well plate (Perkin Elmer, 6007290) in duplicate. After incubating at 25° C. for 15 minutes, 2.5 μL of substrate was added to start the reaction. The plate was incubated at 25° C. for 60 minutes. The final reaction concentrations in the system were: 5 nM BRAF or 1.5 nM cRAF or 5 nM BRAF (V600E), 10 mM ATP, 200 nM MEK1, HEPES 50 mM, EGTA 1 mM, $MgCl_2$ 10 mM, and Brij35 0.01%. The concentrations of the test compounds were: 300, 100, 33.33, 11.11, 3.7, 1.23, 0.412, 0.137, 0.046, 0.015, 0 nM, and the final concentration of DMSO was 1%. Then 10 μL of ADP Glo reagent was added, and further incubated at 25° C. for 40 minutes. Then 20 μL of detection reagent was added, and further incubated at 25° C. for 40 minutes. The enzyme activity in the presence of the compounds at each concentration was then measured by an Envision microplate reader (Perkin Elmer 2104), and the inhibitory activity of the compounds at each concentration against the enzyme activity was calculated. The inhibitory activities of the compounds at different concentrations against the enzyme activity were then fitted using Graphpad 5.0 software according to the four-parameter equation, and the $IC_{50}$ values were calculated.

The compounds of the present disclosure were tested in the above kinase inhibition assay. It was found that, compared with the non-deuterated parent compound Encorafenib, the compounds of the present disclosure have equivalent or even stronger inhibitory effect against BRAF and cRAF kinases, indicating that the compounds of the present disclosure have more potent activity on BRAF V600E mutation. The results of the representative example compounds are summarized in Table 1 below.

TABLE 1

| Example compound | BRAF $IC_{50}$ (nM) | cRAF $IC_{50}$ (nM) | BRAF(V600E) $IC_{50}$ (nM) |
|---|---|---|---|
| Encorafenib | 2.95 | 1.49 | 4.98 |
| L-1 | 3.49 | 2.31 | 3.64 |
| L-2 | 1.57 | 1.36 | 2.43 |
| L-3 | 2.22 | 1.26 | 2.14 |
| L-4-S | 3.77 | 1.66 | 3.58 |
| L-5-S | 7.41 | 3.74 | 11.98 |

(2) Cytotoxicity Assay

A375 is a melanoma cell line with BRAF V600E mutation, and HT-29 is a colorectal cancer cell line with BRAF V600E mutation.

A375 (adherent, number of cells/well: 3000, medium: RPMI-1640+10% FBS) and HT-29 (adherent, number of cells/well: 3000, medium: RPMI-1640+10% FBS) cells in the logarithmic growth phase were harvested. The cell viability was detected by trypan blue exclusion method to ensure that the cell viability was greater than 90%. The cells were inoculated in a 96-well plate and cultured overnight under the condition of 37° C. and 5% $CO_2$. The 10-fold drug solutions were prepared by a 3.16-fold serial dilution starting from a maximum concentration of 1 μM, resulting in 9 concentrations. 10 μL of the drug solutions were added to each well of the 96-well plate in triplicate, and the incubation was further continued for 72 hours. An equal volume of CTG solution was added to each well, and the cell plate w as shaked on an orbital shaker for 5 minutes to lyse the cells. The cell plate was placed at room temperature for 20 minutes to stabilize the luminescence signal, and the luminescence values were then read on a SpectraMax multi-label microplate reader (MD, 2104-0010A). The data were analyzed with GraphPad Prism 5.0 software, and fitted using the non-linear S-curve regression to obtain a dose-effect curve, from which $IC_{50}$ values were calculated accordingly.

The compounds of the present disclosure were tested in the above cytotoxicity assay. It was found that, compared with the non-deuterated parent compound Encorafenib, the compounds of the present disclosure have stronger inhibitory effect on A375 and HT-29, indicating that the compounds of the present disclosure have potent activity on BRAY V600E mutation. The results of the representative example compounds are summarized in Table 2 below.

TABLE 2

| Example compound | A375 $IC_{50}$ (nM) | HT-29 $IC_{50}$ (nM) |
|---|---|---|
| Encorafenib | 4.07 | 8.96 |
| L-1 | 5.33 | 7.74 |
| L-2 | 3.75 | 6.79 |
| L-3 | 3.50 | 7.20 |
| L-4-S | 3.73 | 7.27 |
| L-5-S | 5.58 | 10.46 |

(3) Metabolic Stability Evaluation

Microsome assay: human liver microsomes (HLM): 0.5 mg/mL, Xenotech; rat liver microsomes (RLM): 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solutions: Powders of the example compounds and the control compound were accurately weighed and dissolved in DMSO to 5 mM respectively.

Preparation of phosphate buffer (100 mM, pH 7.4): A pre-prepared 0.5 M potassium dihydrogen phosphate solution (150 mL) was mixed with a pre-prepared 0.5 M dibasic potassium phosphate solution (700 mL). The pH of the mixture was adjusted to 7.4 with a 0.5 M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice before use.

Preparation of stop solution: an acetonitrile solution containing 50 ng/mL propranolol hydrochloride and 200 ng/mL tolbutamide (internal standard). 25057.5 μL of phosphate buffer (pH 7.4) was added into a 50 mL centrifuge tube, to which 812.5 μL of human liver microsomes were then added and mixed well to obtain a liver microsome dilution with a protein concentration of 0.625 mg/mL. 25057.5 μL of phosphate buffer (pH 7.4) was added into a 50 mL centrifuge tube, to which 812.5 μL of SD rat liver microsomes were then added and mixed well to obtain a liver microsome dilution with a protein concentration of 0.625 mg/mL.

Incubation of the samples: The stock solutions of the respective compounds were respectively diluted to 0.25 mM with an aqueous solution containing 70% acetonitrile, and used as a working solution, ready for use. 398 µL of the dilutions of human liver microsomes or rat liver microsomes were added to 96-well incubation plates (N=2), respectively, and 2 µL of 0.25 mM working solution was added respectively and nixed.

Metabolic stability assay: 300 µL of pre-chilled stop solution was added to each well of 96-well deep well plates and placed on ice as stop plates. The 96-well incubation plates and NADPH regeneration system were placed in a 37° C. water bath, shaken at 100 rpm and pre-incubated for 5 min. 80 µL of incubation solution was taken out from each well of the incubation plates, added to the stop plates, mixed well, and replenished with 20 µL of NADPH regeneration system solution. The resulting mixture was used as a 0-min sample. 80 µL of NADPH regeneration system solution was added to each well of the incubation plates to start the reaction and start counting. The corresponding compounds had a reaction concentration of 1 µM and the protein concentration was 0.5 mg/mL. At 10, 30, and 90 minutes of the reaction, respectively, 100 µL of the reaction solutions were taken out, added to the stop plates, and vortexed for 3 minutes to stop the reaction. The stop plates were centrifuged at 5000×g at 4° C. for 10 min. 100 µL of the supernatant was taken out, added to a 96-well plate pre-added with 100 µL of distilled water, mixed well, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percentage of remaining compound versus time, and $t_{1/2}$ and $CL_{int}$ were calculated according to the equation below, where V/M equals to 1/protein concentration.

$$t_{1/2} = -\frac{0.693}{\text{slope}}, \quad CL_{int} = \frac{0.693}{t_{1/2}} \cdot \frac{V}{M}, \quad t_{1/2}(\text{min}); CL_{int}(\mu L/\text{min/mg}).$$

The metabolic stability of the compounds in human and rat liver microsomes was evaluated by simultaneously testing and comparing the compounds of the present disclosure and the non-deuterated compound. The non-deuterated compound Encorafenib was used as a control sample. In the human and rat liver microsome assays, compared with the non-deuterated compound Encorafenib, the compounds of the present disclosure can significantly improve the metabolic stability. The results of the representative example compounds are summarized in Table 3 below.

TABLE 3

| Example compound | HLM | | RLM | |
|---|---|---|---|---|
| | $T_{1/2}$ (min) | CL (µL/min/mg) | $T_{1/2}$ (min) | CL (µL/min/mg) |
| Encorafenib | 80.06 | 17.31 | 79.56 | 17.42 |
| L-1 | 146.35 | 9.47 | 117.22 | 11.82 |
| L-2 | 152.81 | 9.07 | 82.73 | 16.75 |
| L-3 | 284.89 | 4.87 | 122.68 | 11.30 |
| L-4-S | 111.07 | 12.48 | 83.07 | 16.68 |
| L-5-S | 243.77 | 5.69 | 135.57 | 10.22 |

(4) Pharmacokinetic Assay in Rats

Six male Sprague-Dawley rats, 7 to 8 weeks old, weighted approximately 210 g, were divided into 2 groups with 3 rats in each group. The pharmacokinetic differences of the compounds were compared by intravenous or oral administration of a single dose of the compounds (orally 10 mg/kg).

The rats were fed with standard feed and water, and fasted 16 hours before the assay. The drugs were dissolved with PEG400 and dimethyl sulfoxide. The blood samples were collected from eyelids at the time points of 0.083, 0.25, 0.5, 1, 2, 4, 6, 8, 12 and 24 hours after administration.

The rats were anesthetized for a short time after inhaling diethyl ether, and 300 µL of blood samples were collected from eyelids and put into test tubes containing 30 µL of 1% heparin salt solution. The test tubes were dried by baking at 60° C. overnight before use. After the blood sample collection at the last time point, the rats were anesthetized with diethyl ether and sacrificed.

Immediately after the collection of the blood samples, the test tubes were gently inverted at least 5 times to ensure the fully mixing and placed on ice. The blood samples were centrifuged at 4° C., 5000 rpm for 5 minutes to separate the plasma from the red blood cells. 100 µL of plasma was pipetted into a clean plastic centrifuge tube, and the name of the compound and time point were marked. The plasma was stored at −80° C. before analysis, and LC-MS/MS was used to determine the concentration of the compounds disclosed herein in plasma. Pharmacokinetic parameters were calculated based on the plasma drug concentrations of each animal at different time points.

The assay shows that the compounds disclosed herein have better pharmacokinetic properties in animals, and therefore have better pharmacodynamics and therapeutic effects.

The above content is a further detailed description of the present disclosure in combination with specific embodiments, and it cannot be assumed that the specific implementation disclosed herein is limited to these descriptions. For a person of ordinary skill in the art to which the present disclosure pertains, a number of simple deductions or substitutions can be made without departing from the concept disclosed herein, and should all be considered as falling within the protection scope disclosed herein.

The invention claimed is:

1. A compound of:

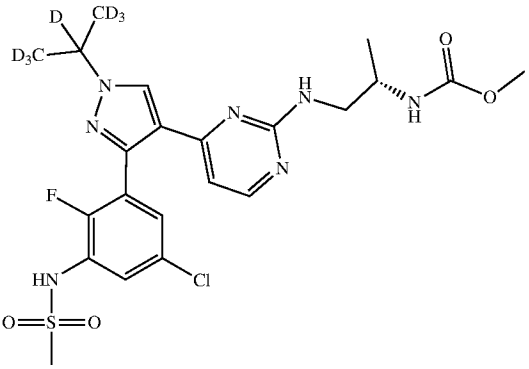 [SMILES: [2H]C([2H])([2H])C([2H])(n1cc(-c2ccnc(NC[C@H](C)NC(=O)OC)n2)c(-c2cc(Cl)cc(NS(C)(=O)=O)c2F)n1)C([2H])([2H])[2H]]

or a tautomer, stereoisomer, prodrug, crystal form, pharmaceutically acceptable salt, hydrate or solvate thereof, wherein each occurrence of the term "D" indicates a $^2$H content of more than 50%.

2. A pharmaceutical composition, comprising pharmaceutically acceptable excipient(s) and the compound, or the tautomer, stereoisomer, prodrug, crystal form, pharmaceutically acceptable salt, hydrate or solvate thereof according to claim 1.

3. The pharmaceutical composition according to claim 2, wherein the pharmaceutical composition further comprises additional therapeutic agent(s).

4. The pharmaceutical composition according to claim 3, wherein the additional therapeutic agent is selected from different BRAF inhibitors, MEK1/2 inhibitors, PI3K inhibitors, CDK4/6 inhibitors, c-Met inhibitors, EGFR inhibitors, FGFR Inhibitors, MAPK inhibitors and ERK inhibitors.

5. A method of treating and/or preventing proliferative diseases caused by BRAF mutations in a subject, comprising administering the compound, or the tautomer, stereoisomer, prodrug, crystal form, pharmaceutically acceptable salt, hydrate or solvate thereof according to claim 1.

6. The method according to claim 5, wherein the BRAF mutation is a V600 mutation.

7. The method according to claim 5, wherein the proliferative disease is melanoma characterized by a BRAF V600 mutation or colorectal cancer characterized by a BRAF V600 mutation.

8. The method according to claim 5, wherein the BRAF mutation is a V600E mutation.

9. The method according to claim 5, wherein the proliferative disease is melanoma characterized by BRAF V600E mutation or colorectal cancer characterized by BRAF V600E mutation.

\* \* \* \* \*

UNITED STATES PATENT AND TRADEMARK OFFICE
CERTIFICATE OF CORRECTION

PATENT NO. : 12,076,320 B2
APPLICATION NO. : 17/259472
DATED : September 3, 2024
INVENTOR(S) : Yihan Wang et al.

Page 1 of 1

It is certified that error appears in the above-identified patent and that said Letters Patent is hereby corrected as shown below:

On the Title Page

Change:
"(71) Applicant: Shenzhen TargetRx, Inc., Guangdong (CN)"
To:
--(71) Applicant: Shenzhen TargetRx, Inc., Shenzhen, Guangdong (CN)--

Change:
"(73) Assignee: Shenzhen TargetRx, Inc., Guangdong (CN)"
To:
--(73) Assignee: Shenzhen TargetRx, Inc., Shenzhen, Guangdong (CN)--

Signed and Sealed this
Twenty-second Day of October, 2024

Katherine Kelly Vidal
*Director of the United States Patent and Trademark Office*